United States Patent
Lin et al.

(10) Patent No.: US 10,745,360 B2
(45) Date of Patent: Aug. 18, 2020

(54) QUINOXALINE COMPOUNDS, METHOD FOR PREPARING THE SAME AND USE THEREOF

(71) Applicants: Development Center for Biotechnology, New Taipei (TW); DCB-USA LLC, Wilmington, DE (US)

(72) Inventors: Nan-Horng Lin, New Taipei (TW); Chu-Bin Liao, New Taipei (TW); Shao-Zheng Peng, New Taipei (TW); Shih-Chieh Yen, New Taipei (TW); Mann-Yan Kuo, New Taipei (TW)

(73) Assignee: Development Center for Biotechnology, New Taipei (TW)

( * ) Notice: Subject to any disclaimer, the term of this patent is extended or adjusted under 35 U.S.C. 154(b) by 0 days.

(21) Appl. No.: 15/326,490

(22) PCT Filed: Jun. 15, 2015

(86) PCT No.: PCT/US2015/035822
§ 371 (c)(1),
(2) Date: Jan. 15, 2017

(87) PCT Pub. No.: WO2016/010662
PCT Pub. Date: Jan. 21, 2016

(65) Prior Publication Data
US 2018/0208561 A1    Jul. 26, 2018

Related U.S. Application Data

(60) Provisional application No. 62/025,212, filed on Jul. 16, 2014.

(51) Int. Cl.
| | | |
|---|---|---|
| *C07D 241/44* | (2006.01) |
| *C07D 401/12* | (2006.01) |
| *A61P 35/00* | (2006.01) |
| *C07D 413/04* | (2006.01) |
| *C07D 413/12* | (2006.01) |
| *A61P 9/00* | (2006.01) |
| *A61P 19/02* | (2006.01) |
| *A61P 3/10* | (2006.01) |
| *A61P 13/12* | (2006.01) |

(52) U.S. Cl.
CPC ............ *C07D 241/44* (2013.01); *A61P 3/10* (2018.01); *A61P 9/00* (2018.01); *A61P 13/12* (2018.01); *A61P 19/02* (2018.01); *A61P 35/00* (2018.01); *C07D 401/12* (2013.01); *C07D 413/04* (2013.01); *C07D 413/12* (2013.01)

(58) Field of Classification Search
CPC .. C07D 241/44; C07D 401/12; C07D 413/04; C07D 413/12; A61P 35/00
See application file for complete search history.

(56) References Cited

FOREIGN PATENT DOCUMENTS

| WO | WO 2006040568 | * | 4/2006 |
| WO | WO2012118492 | * | 9/2012 |

* cited by examiner

*Primary Examiner* — Barbara P Badio
(74) *Attorney, Agent, or Firm* — Liang Legal Group, PLLC

(57) ABSTRACT

A compound for treating a protein kinase-related disease or disorder having a structure of formula (I)

formula (I)

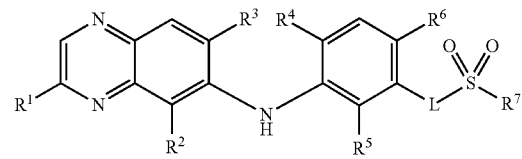

wherein L is $NR^8$ or O; $R^1$, $R^2$, $R^3$, $R^4$, $R^5$, $R^6$ and $R^7$ are defined herein. Compounds of formula (I) are useful for inhibition of protein kinases. Methods of using compounds of formula (I), stereoisomers, tautomers and pharmaceutically acceptable salts thereof, for in vitro, in situ, and in vivo diagnosis, prevention or treatment of such disorders in mammalian cells, or associated pathological conditions are disclosed.

16 Claims, No Drawings

QUINOXALINE COMPOUNDS, METHOD FOR PREPARING THE SAME AND USE THEREOF

BACKGROUND OF INVENTION

Field of the Invention

The present invention relates to novel chemical compounds and methods for their use in therapy and preparation. In particular, the invention relates to certain substituted quinoxaline compounds and to the use for their inhibition, regulation and/or modulation of particular kinases and their related signal transduction pathways.

Background Art

Protein kinases (PKs) play important roles in cellular signal transduction pathways that regulate various cell functions, such as differentiation, proliferation, migration, survival, and apoptosis. These enzymes catalyze the transfer of a phosphate group from ATP to a tyrosine, serine or threonine residue on a protein substrate. The phosphorylation by kinase and dephosphorylation by phosphatase are involved in countless cellular processes that respond to diverse intracellular or extracellular signals, regulation of cellular functions, and activation or deactivation of cellular operations.

Abnormal PK activity has been linked to cancer as well as metabolic, immunological, and nervous system disorders. Therefore, protein kinases are attractive therapeutic targets for human disease interventions. PK inhibitors, i.e., compounds that block the activities of PKs, have been developed and used widely for clinical applications. While more than thirty PK inhibitors have been approved for use in disease treatments, such as cancer therapy, there is still a need for new PK inhibitors to treat various disorders or to overcome drug-resistance. The identification of effective small molecule compounds that can specifically inhibit signal transduction and cellular proliferation, by modulating PK activity to regulate and modulate inappropriate cell proliferation, differentiation, or metabolism that is essential for processes leading to cancer, would be beneficial.

SUMMARY OF INVENTION

Embodiments of the invention are based on unexpected findings that certain quinoxaline compounds can inhibit activities of protein kinase (e.g., B-Raf, B-Raf$^{V600E}$, C-Raf). These properties allow these quinoxaline compounds to be used in treating protein kinase-related diseases including cancers.

In one aspect, embodiments of the invention relate to quinoxaline compounds of formula (I)

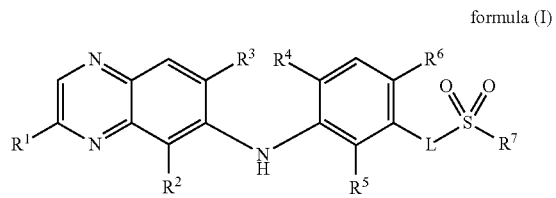

formula (I)

or stereoisomers or pharmaceutically acceptable salts thereof, wherein L is NR$^8$ or O, and R$^1$, R$^2$, R$^3$, R$^4$, R$^5$, R$^6$, and R$^7$ are as defined below.

In accordance with any of the above-described embodiments, R$^1$ in formula (I) is selected from the group consisting of hydrogen, halogen, NR$^9$R$^{10}$, OR$^{11}$, C$_1$-C$_6$ alkyl, C$_2$-C$_6$ alkenyl, C$_2$-C$_6$ alkynyl, C$_1$-C$_6$ alkoxy, C$_3$-C$_6$ cycloalkyl, phenyl, a 3-to-6 membered heterocyclyl, and a 5-to-6 membered heteroaryl, wherein the alkyl, alkenyl, alkynyl, cycloakyl, phenyl, heterocyclyl, and heteroaryl may be optionally substituted with halogen, oxo (except for phenyl or heteroaryl), OR$^a$, SR$^a$, NR$^b$R$^c$, phenyl, C$_1$-C$_4$ alkyl, C$_1$-C$_4$ alkoxy, and cyclopropyl, wherein the alkyl, alkoxy, and cyclopropyl may be optionally substituted with R$^d$, wherein R$^9$, R$^{10}$, R$^{11}$, R$^a$, R$^b$, R$^c$, and R$^d$ are independently as defined below.

In accordance with any of the above-described embodiments, R$^2$ in formula (I) is selected from the group consisting of hydrogen, halogen, nitro, CN, OR$^{11}$, COR$^{12}$, and NR$^{13}$R$^{14}$, provided that R$^2$ is hydrogen or halogen only when R$^1$ is NR$^9$R$^{10}$, wherein R$^9$, R$^{10}$, R$^{11}$, R$^{12}$, R$^{13}$, are independently as defined below.

In accordance with any of the above-described embodiments, R$^3$ in formula (I) is selected from the group consisting of hydrogen, halogen, hydroxy, azido, cyano, nitro, C$_2$-C$_6$ alkenyl, C$_2$-C$_6$ alkynyl, C$_3$-C$_6$ cycloalkyl, phenyl, a 3-to-6 membered heterocyclyl, and a 5-to-6 membered heteroaryl, wherein the alkyl, alkenyl, alkynyl, cycloakyl, phenyl, heterocyclyl, and heteroaryl may be optionally substituted with halogen, oxo (except for phenyl or heteroaryl), OR$^a$, SR$^a$, NR$^b$R$^c$, phenyl, C$_1$-C$_4$ alkyl, C$_1$-C$_4$ alkoxy, and cyclopropyl, wherein the alkyl, alkoxy, and cyclopropyl may be optionally substituted with R$^d$, provided that R$^3$ is hydrogen or halogen only when R$^1$ is NR$^9$R$^{10}$, wherein R$^a$, R$^b$, R$^c$, R$^9$, and R$^{10}$ are independently as defined below.

In accordance with any of the above-described embodiments, R$^4$, R$^5$ and R$^6$ in formula (I) are independently selected from the group consisting of hydrogen, halogen, hydroxyl, amino, CN, C$_1$-C$_4$ alkyl, alkoxy C$_1$-C$_4$ alkoxy, dialkylamino, C$_1$-C$_4$ alkoxy, and heterocyclyl.

In accordance with any of the above-described embodiments, R$^7$ in formula (I) is C$_1$-C$_4$ alkyl, C$_1$-C$_4$ haloalkyl, or aryl.

In accordance with any of the above-described embodiments, R$^8$ is selected from the group consisting of hydrogen, SO$_2$R$^{15}$, C$_1$-C$_6$ alkyl, C$_2$-C$_6$ alkenyl, C$_2$-C$_6$ alkynyl, C$_3$-C$_6$ cycloalkyl, and a 3-to-6 membered heterocyclyl, wherein the alkyl, alkenyl, alkynyl, cycloakyl and heterocyclyl may be optionally substituted with halogen, oxo (except for phenyl or heteroaryl), OR$^a$, SR$^a$, NR$^b$R$^c$, phenyl, C$_1$-C$_4$ alkyl, C$_1$-C$_4$ alkoxy, and cyclopropyl, wherein the alkyl, alkoxy, and cyclopropyl may be optionally substituted with R$^d$, wherein R$^{15}$, R$^a$, R$^b$, R$^c$, and R$^d$ are independently as defined below.

In accordance with any of the above-described embodiments, R$^9$ and R$^{10}$ are independently selected from the group consisting of hydrogen, COR$^{15}$, SO$_2$R$^{15}$, OR$^{16}$, NR$^{17}$R$^{18}$, C$_1$-C$_6$ alkyl, C$_2$-C$_6$ alkenyl, C$_2$-C$_6$ alkynyl, C$_3$-C$_6$ cycloalkyl, phenyl, a 3-to-6 membered heterocyclyl, and a 5-to-6 membered heteroaryl, wherein the alkyl, alkenyl, alkynyl, cycloakyl, phenyl, heterocyclyl, and heteroaryl may be optionally substituted with halogen, oxo (except for phenyl or heteroaryl), OR$^a$, SR$^a$, NR$^b$R$^c$, phenyl, C$_1$-C$_4$ alkyl, C$_1$-C$_4$ alkoxy, and cyclopropyl, wherein the alkyl, alkoxy, and cyclopropyl may be optionally substituted with R$^d$, provided that R$^2$ and R$^3$ are independently selected from hydrogen or halogen only when R$^9$ and R$^{10}$ are not hydrogen or C$_1$-C$_4$ alkyl, wherein R$^{15}$, R$^{16}$, R$^{17}$, R$^{18}$, R$^a$, R$^b$, R$^c$, and R$^d$ are independently as defined below.

Alternatively, $R^9$ and $R^{10}$, together with the nitrogen atom to which they are attached, may form a 3-to-6 membered heterocyclyl, which may be optionally substituted by halogen, oxo or $C_1$-$C_3$ alkyl.

In accordance with any of the above-described embodiments, $R^{11}$ is selected from the group consisting of hydrogen, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, phenyl, a 3-to-6 membered heterocyclyl, and a 5-to-6 membered heteroaryl, wherein the alkyl, alkenyl, alkynyl, cycloakyl, phenyl, heterocyclyl, and heteroaryl may be optionally substituted with halogen, oxo (except for phenyl or heteroaryl), $OR^a$, $SR^a$, $NR^bR^c$, phenyl, $C_1$-$C_4$ alkyl, $C_1$-$C_4$ alkoxy, and cyclopropyl, wherein the alkyl, alkoxy, and cyclopropyl may be optionally substituted with $R^d$, wherein $R^a$, $R^b$, $R^c$, and $R^d$ are independently as defined below.

In accordance with any of the above-described embodiments, $R^{12}$ is selected from the group consisting of hydrogen, $OR^{19}$, $NR^{20}R^{21}$, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, phenyl, a 3-to-6 membered heterocyclyl, and a 5-to-6 membered heteroaryl, wherein the alkyl, alkenyl, alkynyl, cycloakyl, phenyl, heterocyclyl, and heteroaryl may be optionally substituted with halogen, oxo (except for phenyl or heteroaryl), $OR^a$, $SR^a$, $NR^bR^c$, phenyl, $C_1$-$C_4$ alkyl, $C_1$-$C_4$ alkoxy, and cyclopropyl, wherein the alkyl, alkoxy, and cyclopropyl may be optionally substituted with $R^d$, wherein $R^{19}$, $R^{20}$, $R^{21}$, $R^a$, $R^b$, $R_c$, and $R^d$ are independently as defined below.

In accordance with any of the above-described embodiments, $R^{13}$ and $R^{14}$ are independently selected from the group consisting of hydrogen, $COR^{15}$, $SO_2R^{15}$, $C_1$-$C_6$ alkyl, $C_2$-$C_6$ alkenyl, $C_2$-$C_6$ alkynyl, $C_3$-$C_6$ cycloalkyl, phenyl, a 3-to-6 membered heterocyclyl, and a 5-to-6 membered heteroaryl, wherein the alkyl, alkenyl, alkynyl, cycloakyl, phenyl, heterocyclyl, and heteroaryl may be optionally substituted with halogen, oxo (except for phenyl or heteroaryl), $OR^a$, $SR^a$, $NR^bR^c$, phenyl, $C_1$-$C_4$ alkyl, $C_1$-$C_4$ alkoxy, and cyclopropyl, wherein the alkyl, alkoxy, and cyclopropyl may be optionally substituted with $R^d$, wherein $R^{15}$, $R^a$, $R^b$, $R^c$, and $R^d$ are independently as defined below.

In accordance with any of the above-described embodiments, $R^{15}$ is selected from the group consisting of $C_1$-$C_4$ alkyl, $C_1$-$C_4$ haloalkyl, and aryl.

In accordance with any of the above-described embodiments, $R^{16}$ is selected from the group consisting of hydrogen, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, phenyl, a 3-to-6 membered heterocyclyl, and a 5-to-6 membered heteroaryl, wherein the alkyl, alkenyl, alkynyl, cycloakyl, phenyl, heterocyclyl, and heteroaryl may be optionally substituted with halogen, oxo (except for phenyl or heteroaryl), $OR^a$, $SR^a$, $NR^bR^c$, phenyl, $C_1$-$C_4$ alkyl, $C_1$-$C_4$ alkoxy, and cyclopropyl, wherein the alkyl, alkoxy, and cyclopropyl may be optionally substituted with $R^d$, wherein $R^a$, $R^b$, $R^c$, and $R^d$ are independently as defined below.

In accordance with any of the above-described embodiments, $R^{17}$ and $R^{18}$ are independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, phenyl, a 3-to-6 membered heterocyclyl, and a 5-to-6 membered heteroaryl, wherein the alkyl, alkenyl, alkynyl, cycloakyl, phenyl, heterocyclyl, and heteroaryl may be optionally substituted with halogen, oxo (except for phenyl or heteroaryl), $OR^a$, $SR^a$, $NR^bR^c$, phenyl, $C_1$-$C_4$ alkyl, $C_1$-$C_4$ alkoxy, and cyclopropyl, wherein the alkyl, alkoxy, and cyclopropyl may be optionally substituted with $R^d$, wherein $R^a$, $R^b$, $R^c$, and $R^d$ are independently as defined below.

In accordance with any of the above-described embodiments, $R^{19}$ is selected from the group consisting of hydrogen, $C_1$-$C_4$ alkyl, $C_1$-$C_4$ haloalkyl, and aryl.

In accordance with any of the above-described embodiments, $R^{20}$ and $R^{21}$ are independently selected from the group consisting of hydrogen, $C_1$-$C_4$ alkyl, $C_1$-$C_4$ haloalkyl, and aryl.

In accordance with any of the above-described embodiments, each $R^a$ is independently hydrogen or $C_1$-$C_4$ alkyl.

In accordance with any of the above-described embodiments, each $R^b$ and $R^c$ are independently selected from the group consisting of hydrogen, $SO_2R^7$ and $C_1$-$C_4$ alkyl, wherein $C_1$-$C_4$ alkyl may be optionally substituted with halogen, wherein $R^7$ is as defined above.

In accordance with any of the above-described embodiments, each $R^d$ is independently selected from the group consisting of halogen, oxo, $C_1$-$C_4$ alkyl, and $C_1$-$C_4$ alkoxyl, wherein the $C_1$-$C_4$ alkyl and $C_1$-$C_4$ alkoxyl may be optionally substituted with halogen.

Preferred embodiments of the present invention relate to a compound selected from the group consisting of N1-3-[(3-{2,6-difluoro-3-[(propylsulfonyl)amino]anilino}-6-quinoxalinyl)amino]-2,4-difluorophenyl-1-propanesulfonamide; N1-(3-{[3-(2,6-difluoro anilino)-6-quinoxalinyl] amino}-2,4-difluorophenyl)-1-propanesulfonamide; N1-{3-[(5-amino-3-methoxy-6-quinoxalinyl)amino]-2,4-difluorophenyl}-1-propanesulfonamide; N1-{2,4-difluoro-3-[(3-methoxy-5-nitro-6-quinoxalinyl)amino]phenyl}-1-propanesulfonamide; N1-{2,4-difluoro-3-[(3-methoxy-5-nitro-6-quinoxalinyl)amino]phenyl}-3-fluoro-1-propane sulfonamide; N1-(2,4-difluoro-3-{[3-(2-morpholinoethoxy)-5-nitro-6-quinoxalinyl]amino}phenyl)-1-propanesulfonamide; N1-(2,4-difluoro-3-[3-(2-methoxyethoxy)-5-nitro-6-quinoxalinyl]aminophenyl)-1-propanesulfonamide; N1-(7-{2,6-difluoro-3-[(propylsulfonyl)amino]anilino}-2-quinoxalinyl)-1-cyclopropanecarboxamide; N1-[3-({3-[2-(dimethylamino)ethoxy]-5-nitro-6-quinoxalinyl}amino)-2,4-difluorophenyl]-1-propanesulfonamide; N1-{3-[(5-cyano-3-methoxy-6-quinoxalinyl)amino]-2,4-difluorophenyl}1-propanesulfonamide; N1-(2,4-difluoro-3-{[3-(2-fluoroanilino)-6-quinoxalinyl]amino}phenyl)-1-propanesulfonamide; N1-(2,4-difluoro-3-{[3-(3-pyridylamino)-6-quinoxalinyl]amino}phenyl)-1-propanesulfonamide; N1-{3-{[3-(2,4-difluoroanilino)-6-quinoxalinyl]amino}-2,4-difluorophenyl)-1-propanesulfonamide; N-{2,4-difluoro-3-[(3-methoxy-5-nitro-6-quinoxalinyl)amino]phenyl}methanesulfonamide; N1-{3-[(5-cyano-3-hydroxy-6-quinoxalinyl)amino]-2,4-difluorophenyl}-1-propanesulfonamide; N1-(3-{[5-cyano-3-(2-morpholinoethoxy)-6-quinoxalinyl]amino)-2,4-difluorophenyl)-1-propanesulfonamide; N-(3-(5-cyano-3-ethoxyquinoxalin-6-ylamino)-2,4-difluorophenyl)propane-1-sulfonamide; N-(3-(5-cyano-3-(dimethylamino)quinoxalin-6-ylamino)-2,4-difluorophenyl)propane-1-sulfonamide; N-(3-(5-cyano-3-morpholinoquinoxalin-6-ylamino)-2,4-difluorophenyl)propane-1-sulfonamide; N-(3-(5-cyano-3-(methylamino)quinoxalin-6-ylamino)-2,4-difluorophenyl)propane-1-sulfonamide; N-(3-(5-cyano-3-methoxyquinoxalin-6-ylamino)-2,6-difluorophenyl) propane-1-sulfonamide; N-(5-(5-cyano-3-methoxyquinoxalin-6-ylamino)-2-fluorophenyl) propane-1-sulfonamide; N-(3-(5-cyano-3-morpholinoquinoxalin-6-ylamino)-4-fluorophenyl) propane-1-sulfonamide; N-(3-(5-cyano-3-ethoxyquinoxalin-6-ylamino)-4-fluorophenyl) benzenesulfonamide; N-(3-(5-cyano-3-morpholinoquinoxalin-6-ylamino)-4-fluorophenyl) benzenesulfonamide; N-(3-(5-cyano-3-morpholinoquinoxalin-6-ylamino)-4-fluorophenyl)

methanesulfonamide; N-(3-(5-cyano-3-ethoxyquinoxalin-6-ylamino)-4-fluorophenyl) methanesulfonamide; N-(3-(5-cyano-3-(dimethylamino)quinoxalin-6-ylamino)-4-fluorophenyl)propane-1-sulfonamide; N-(2,4-difluoro-3-(5-formyl-3-methoxyquinoxalin-6-ylamino)phenyl)propane-1-sulfonamide; 6-(2,6-difluoro-3-(propylsulfonamido) phenylamino)-3-methoxyquinoxaline-5-carboxylic acid; methyl 6-(2,6-difluoro-3-(propylsulfonamido)phenylamino)-3-methoxyquinoxaline-5-carboxylate; N-(2,4-difluoro-3-(3-methoxy-7-methylquinoxalin-6-ylamino)phenyl)propane-1-sulfonamide; N-(3-(5-cyano-3-morpholinoquinoxalin-6-ylamino)-2,4-difluorophenyl)-3-fluoropropane-1-sulfonamide; N-(3-(5-cyano-3-ethoxyquinoxalin-6-ylamino)-2,4-difluorophenyl)-3-fluoropropane-1-sulfonamide; N-(3-(5-cyano-3-methoxyquinoxalin-6-ylamino)-4-fluorophenyl) benzenesulfonamide; N-(3-(5-cyano-3-ethoxyquinoxalin-6-ylamino)-4-fluorophenyl)propane-1-sulfonamide; N-(3-(5-cyano-3-(dimethylamino)quinoxalin-6-ylamino)-4-fluorophenyl)benzenesulfonamide; N-(3-(5-cyano-3-morpholinoquinoxalin-6-ylamino)-2-methylphenyl) propane-1-sulfonamide; N-(3-(5-cyano-3-morpholinoquinoxalin-6-ylamino)-4-methylphenyl) propane-1-sulfonamide; N-(3-(5-cyano-3-methoxyquinoxalin-6-ylamino)-4-methylphenyl)propane-1-sulfonamide; N-(3-(5-cyano-3-methoxyquinoxalin-6-ylamino)-4-fluorophenyl)methanesulfonamide; N-(3-(5-cyano-3-methoxyquinoxalin-6-ylamino)-2,4-difluorophenyl)-N-ethylpropane-1-sulfonamide; N-(3-(5-cyano-3-methoxyquinoxalin-6-ylamino)-2,4-difluorophenyl)-N-methylpropane-1-sulfonamide; N-(3-(5-cyano-3-methoxyquinoxalin-6-ylamino)-2-methylphenyl) propane-1-sulfonamide; N-(5-(5-cyano-3-methoxyquinoxalin-6-ylamino)-2-methylphenyl) propane-1-sulfonamide; N-(2-chloro-3-(5-cyano-3-methoxyquinoxalin-6-ylamino)-4-fluorophenyl)propane-1-sulfonamide; N-(2-chloro-3-(5-cyano-3-methoxyquinoxalin-6-ylamino)-4-fluorophenyl) benzenesulfonamide; N-(2-chloro-3-(5-cyano-3-morpholinoquinoxalin-6-ylamino)-4-fluorophenyl)propane-1-sulfonamide; N-(2-chloro-3-(5-cyano-3-morpholinoquinoxalin-6-ylamino)-4-fluorophenyl) benzenesulfonamide; and N-(2-cyano-3-(5-cyano-3-methoxyquinoxalin-6-ylamino)phenyl) propane-1-sulfonamide.

Another aspect of the present invention relates to methods for preventing or treating a disease or disorder modulated/mediated by or related to a protein kinase. The kinase may include, but are not limited to, B-Raf, B-Raf$^{V600E}$, C-Raf, MEK1, etc. An exemplary method for preventing or treating a disease or disorder modulated/mediated by or related to a protein kinase comprises administering to a subject (such as, mammal) in need of such treatment an effective amount of a compound of this invention or a stereoisomer, tautomer, solvate, prodrug or pharmaceutically acceptable salt thereof. Examples of such diseases and disorders include, but are not limited to, hyperproliferative disorders (such as cancer, including melanoma and other cancers of the skin), neurodegeneration, cardiac hypertrophy, pain, migraine and neurotraumatic disease, kidney diseases (such as polycystic kidney disease), etc.

Another aspect of the present invention provides the use of a compound of this invention in the manufacture of a medicament for the treatment of a hyperproliferative disease. In a further embodiment, the hyperproliferative disease may be cancer (or still further, a specific cancer as defined herein).

Another aspect of the present invention provides the use of a compound of this invention in the manufacture of a medicament for the treatment of a protein kinase associated disease or disorder, such as hyperproliferative disorders (such as cancer, including melanoma and other cancers of the skin), neurodegeneration, cardiac hypertrophy, pain, migraine and neurotraumatic disease, kidney diseases (such as polycystic kidney disease). The protein kinase may be B-Raf, and the medicament is an inhibitor of B-Raf.

Another aspect of the present invention provides a pharmaceutical composition comprising a compound of this invention, a stereoisomer, tautomer, solvate, prodrug or a pharmaceutically acceptable salt thereof, and a pharmaceutically acceptable carrier or excipient.

Other aspects and advantages of the invention will be apparent from the following description and the appended claims.

DETAILED DESCRIPTION

Definition

Reference will now be made in detail to certain embodiments, examples of which are illustrated in the accompanying structures and formulas. While enumerated embodiments will be described, it will be understood that they are not intended to limit the invention to those embodiments. On the contrary, the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature and similar materials differs from or contradicts this application, including but not limited to defined terms, term usage, described techniques, or the like, this application controls.

The term "alkyl" refers to a straight or branched monovalent saturated hydrocarbon containing, unless otherwise stated, 1-20 carbon atoms. The numerical ranges in this description are intended to include any number(s) in the defined range, as if the individual numbers have been separately disclosed. For example, an alkyl group of 1-20 carbons would include $C_1$, $C_2$, . . . $C_{20}$, as well as $C_1$-$C_{20}$, $C_1$-$C_{15}$, $C_1$-$C_{10}$, $C_1$-$C_6$, $C_1$-$C_4$, etc. Examples of alkyl include, but are not limited to, methyl, ethyl, n-propyl, i-propyl, n-butyl, i-butyl, and t-butyl.

The term "alkenyl" refers to a straight or branched monovalent hydrocarbon containing 2-20 carbon atoms (e.g., $C_2$-$C_{10}$) and one or more double bonds. Examples of alkenyl include, but are not limited to, ethenyl, propenyl, allyl, and 1,4-butadienyl.

The term "alkynyl" refers to a straight or branched monovalent hydrocarbon containing 2-20 carbon atoms (e.g., $C_2$-$C_{10}$) and one or more triple bonds. Examples of alkynyl include, but are not limited to, ethynyl, 1-propynyl, 1- and 2-butynyl, and 1-methyl-2-butynyl.

The term "alkoxy" refers to an —O-alkyl radical, wherein the alkyl portion is as defined above. Examples of alkoxy include, but are not limited to, methoxy, ethoxy, n-propoxy, iso-propoxy, n-butoxy, iso-butoxy, sec-butoxy, and tert-butoxy.

The term "acyloxy" refers to an —O—C(O)—R radical in which R can be H, alkyl, alkenyl, alkynyl, cycloalkyl, cycloalkenyl, heterocycloalkyl, heterocycloalkenyl, aryl, or heteroaryl.

The term "amino" refers to $NH_2$. The term "alkylamino" refers to an —N(R)-alkyl radical in which R can be H, alkyl, alkenyl, alkynyl, cycloalkyl, cycloalkenyl, heterocycloalkyl, heterocycloalkenyl, aryl, or heteroaryl.

The term "cycloalkyl" refers to a monovalent saturated hydrocarbon ring system having 3 to 30 carbon atoms (e.g., $C_3$-$C_6$ or $C_3$-$C_{12}$). Examples of cycloalkyl include, but are not limited to, cyclopropyl, cyclobutyl, cyclopentyl, cyclohexyl, cycloheptyl, cyclooctyl, and adamantanyl.

The term "cycloalkenyl" refers to a monovalent non-aromatic hydrocarbon ring system having 3 to 30 carbons (e.g., $C_3$-$C_6$ or $C_3$-$C_{12}$) and one or more double bonds. Examples include cyclopentenyl, cyclohexenyl, and cycloheptenyl.

The term "heterocycloalkyl" refers to a monovalent non-aromatic 5-8 membered monocyclic, 8-12 membered bicyclic, or 11-14 membered tricyclic ring system having one or more heteroatoms (such as O, N, S, or Se). Examples of heterocycloalkyl groups include, but are not limited to, piperazinyl, pyrrolidinyl, piperidinyl, dioxanyl, morpholinyl, and tetrahydrofuranyl.

The term "heterocycloalkenyl" refers to a monovalent nonaromatic 5-8 membered monocyclic, 8-12 membered bicyclic, or 11-14 membered tricyclic ring system having one or more heteroatoms (such as O, N, S, or Se) and one or more double bonds.

The term "aryl" refers to a monovalent 6-carbon monocyclic, 10-carbon bicyclic, or 14-carbon tricyclic aromatic ring system. Examples of aryl groups include, but are not limited to, phenyl, naphthyl, and anthracenyl.

The term "aryloxyl" refers to an —O-aryl. The term "arylamino" refers to an —N(R)-aryl, wherein R can be H, alkyl, alkenyl, alkynyl, cycloalkyl, cycloalkenyl, heterocycloalkyl, heterocycloalkenyl, aryl, or heteroaryl. The term "heteroaryl" refers to a monovalent aromatic 5-8 membered monocyclic, 8-12 membered bicyclic, or 11-14 membered tricyclic ring system having one or more heteroatoms (such as O, N, S, or Se). Examples of heteroaryl groups include pyridyl, furyl, imidazolyl, benzimidazolyl, pyrimidinyl, thienyl, quinolinyl, indolyl, thiazolyl, pyrrolyl, isoquinolinyl, purinyl, oxazolyl, pyrazolyl, and carbazolyl. In all these terms, "aryl" portion is as defined above.

The term "halogen" refers to F, Cl, Br or I.

The bove-described alkyl, alkenyl, alkynyl, cycloalkyl, heterocycloalkyl, cycloalkenyl, heterocycloalkenyl, amino, alkylamino, arylamino, alkoxy, aryloxy, aryl, and heteroaryl may be substituted or unsubstituted moieties. Possible substituents on amino, alkylamino, arylamino, alkoxy, aryloxy, cycloalkyl, heterocycloalkyl, cycloalkenyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, arylamino, hydroxy, halo, oxo (O=), thioxo (S=), thio, $C_1$-$C_{10}$ alkylthio, arylthio, $C_1$-$C_{10}$ alkylsulfonyl, arylsulfonyl, acylamino, aminoacyl, aminothioacyl, amidino, mercapto, amido, thioureido, thiocyanato, sulfonamido, guanidine, ureido, cyano, nitro, acyl, thioacyl, acyloxy, carbamido, carbamyl (—C(O)$NH_2$), carboxyl (—COOH), and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

Raf Inhibitors

Provided herein are compounds, and pharmaceutical compositions thereof, that are useful in the treatment or prevention of diseases, conditions and/or disorders modulated/mediated by (or associated with) a protein kinase, such as B-Raf.

One embodiment provides compounds of Formula I:

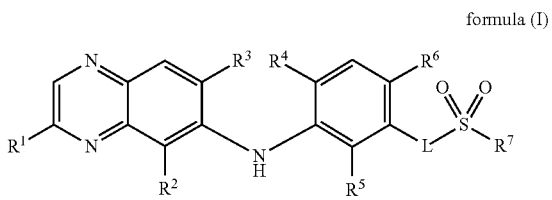

formula (I)

or stereoisomers, tautomers, solvates, prodrugs and pharmaceutically acceptable salts thereof, wherein:

L is $NR^8$ or O;

$R^1$ is selected from the group consisting of hydrogen, halogen, $NR^9R^{10}$, $OR^{11}$, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, phenyl, a 3-to-6 membered heterocyclyl, and a 5-to-6 membered heteroaryl, wherein the alkyl, alkenyl, alkynyl, cycloakyl, phenyl, heterocyclyl, and heteroaryl may be optionally substituted with halogen, oxo (except for phenyl or heteroaryl), $OR^a$, $SR^a$, $NR^bR^c$, phenyl, $C_1$-$C_4$ alkyl, $C_1$-$C_4$ alkoxy, and cyclopropyl, wherein the alkyl, alkoxy, and cyclopropyl may be optionally substituted with $R^d$;

$R^2$ is selected from the group consisting of hydrogen, halogen, nitro, CN, $OR^{11}$, $COR^{12}$, and $NR^{13}R^{14}$, provided that $R^2$ is hydrogen or halogen only when $R^1$ is $NR^9R^{10}$;

$R^3$ is selected from the group consisting of hydrogen, halogen, hydroxy, azido, cyano, nitro, $C_2$-$C_6$ alkenyl, $C_2$-$C_6$ alkynyl, $C_3$-$C_6$ cycloalkyl, phenyl, a 3-to-6 membered heterocyclyl, and a 5-to-6 membered heteroaryl, wherein the alkyl, alkenyl, alkynyl, cycloakyl, phenyl, heterocyclyl, and heteroaryl may be optionally substituted with halogen, oxo (except for phenyl or heteroaryl), $OR^a$, $SR^a$, $NR^bR^c$, phenyl, $C_1$-$C_4$ alkyl, $C_1$-$C_4$ alkoxy, and cyclopropyl, wherein the alkyl, alkoxy, and cyclopropyl may be optionally substituted with $R^d$, provided that $R^3$ is hydrogen or halogen only when $R^1$ is $NR^9R^{10}$;

$R^4$, $R^5$ and $R^6$ are independently selected from the group consisting of hydrogen, halogen, hydroxyl, amino, CN, $C_1$-$C_4$ alkyl, alkoxy $C_1$-$C_4$ alkoxy, dialkylamino, $C_1$-$C_4$ alkoxy, and heterocyclyl;

$R^7$ is $C_1$-$C_4$ alkyl, $C_1$-$C_4$ haloalkyl, or aryl;

$R^8$ is selected from the group consisting of hydrogen, $SO_2R^{15}C_1$-$C_6$ alkyl, $C_2$-$C_6$ alkenyl, $C_2$-$C_6$ alkynyl, $C_3$-$C_6$ cycloalkyl, and a 3-to-6 membered heterocyclyl, wherein the alkyl, alkenyl, alkynyl, cycloakyl, and heterocyclyl may be optionally substituted with halogen, oxo (except for phenyl or heteroaryl), $OR^a$, $SR^a$, $NR^bR^c$, phenyl, $C_1$-$C_4$ alkyl, $C_1$-$C_4$ alkoxy, and cyclopropyl, wherein the alkyl, alkoxy, and cyclopropyl may be optionally substituted with $R^d$;

$R^9$ and $R^{10}$ are independently selected from the group consisting of hydrogen, $COR^{15}$, $SO_2R^{15}$, $OR^{16}$, $NR^{17}R^{18}$, $C_1$-$C_6$ alkyl, $C_2$-$C_6$ alkenyl $C_2$-$C_6$ alkynyl, $C_3$-$C_6$ cycloalkyl, phenyl, a 3-to-6 membered heterocyclyl, and a 5-to-6 membered heteroaryl, wherein the alkyl, alkenyl, alkynyl, cycloakyl, phenyl, heterocyclyl, and heteroaryl may be optionally substituted with halogen, oxo (except for phenyl or heteroaryl), $OR^a$, $SR^a$, $NR^bR^c$, phenyl, $C_1$-$C_4$ alkyl, $C_1$-$C_4$ alkoxy, and cyclopropyl, wherein the alkyl, alkoxy, and cyclopropyl may be optionally substituted with $R^d$, provided that $R^2$ and $R^3$ are independently selected from hydrogen or halogen only when $R^9$ and $R^{10}$ are not hydrogen or $C_1$-$C_4$ alkyl;

$R^9$ and $R^{10}$, together with the nitrogen atom to which they are attached, form a 3-to-6 membered heterocyclyl, which may be optionally substituted by halogen, oxo or $C_1$-$C_3$ alkyl;

$R^{11}$ is selected from the group consisting of hydrogen, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, phenyl, a 3-to-6 membered heterocyclyl, and a 5-to-6 membered heteroaryl, wherein the alkyl, alkenyl, alkynyl, cycloakyl, phenyl, heterocyclyl, and heteroaryl may be optionally substituted with halogen, oxo (except for phenyl or heteroaryl), $OR^a$, $SR^a$, $NR^bR^c$, phenyl, $C_1$-$C_4$ alkyl, $C_1$-$C_4$ alkoxy, and cyclopropyl, wherein the alkyl, alkoxy, and cyclopropyl may be optionally substituted with $R^d$;

$R^{12}$ is selected from the group consisting of hydrogen, $OR^{19}$, $NR^{20}R^{21}$, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, phenyl, a 3-to-6 membered heterocyclyl, and a 5-to-6 membered heteroaryl, wherein the alkyl, alkenyl, alkynyl, cycloakyl, phenyl, heterocyclyl, and heteroaryl may be optionally substituted with halogen, oxo (except for phenyl or heteroaryl), $OR^a$, $SR^a$, $NR^bR^c$, phenyl, $C_1$-$C_4$ alkyl, $C_1$-$C_4$ alkoxy, and cyclopropyl, wherein the alkyl, alkoxy, and cyclopropyl may be optionally substituted with $R^d$, $R^{13}$ and $R^{14}$ are independently selected from the group consisting of hydrogen, $COR^{15}$, $SO_2R^{15}$, $C_1$-$C_6$ alkyl, $C_2$-$C_6$ alkenyl, $C_2$-$C_6$ alkynyl, $C_3$-$C_6$ cycloalkyl, phenyl, a 3-to-6 membered heterocyclyl, and a 5-to-6 membered heteroaryl, wherein the alkyl, alkenyl, alkynyl, cycloakyl, phenyl, heterocyclyl, and heteroaryl may be optionally substituted with halogen, oxo (except for phenyl or heteroaryl), $OR^a$, $SR^a$, $NR^bR^c$, phenyl, $C_1$-$C_4$ alkyl, $C_1$-$C_4$ alkoxy, and cyclopropyl, wherein the alkyl, alkoxy, and cyclopropyl may be optionally substituted with $R^d$;

$R^{15}$ is selected from the group consisting of $C_1$-$C_4$ alkyl, $C_1$-$C_4$ haloalkyl, and aryl;

$R^{16}$ is selected from the group consisting of hydrogen, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, phenyl, a 3-to-6 membered heterocyclyl, and a 5-to-6 membered heteroaryl, wherein the alkyl, alkenyl, alkynyl, cycloakyl, phenyl, heterocyclyl, and heteroaryl may be optionally substituted with halogen, oxo (except for phenyl or heteroaryl), $OR^a$, $SR^a$, $NR^bR^c$, phenyl, $C_1$-$C_4$ alkyl, $C_1$-$C_4$ alkoxy, and cyclopropyl, wherein the alkyl, alkoxy, and cyclopropyl may be optionally substituted with $R^d$;

$R^{17}$ and $R^{18}$ are independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, phenyl, a 3-to-6 membered heterocyclyl, and a 5-to-6 membered heteroaryl, wherein the alkyl, alkenyl, alkynyl, cycloakyl, phenyl, heterocyclyl, and heteroaryl may be optionally substituted with halogen, oxo (except for phenyl or heteroaryl), $OR^a$, $SR^a$, $NR^bR^c$, phenyl, $C_1$-$C_4$ alkyl, $C_1$-$C_4$ alkoxy, and cyclopropyl, wherein the alkyl, alkoxy, and cyclopropyl may be optionally substituted with $R^d$, $R^{19}$ is selected from the group consisting of hydrogen, $C_1$-$C_4$ alkyl, $C_1$-$C_4$ haloalkyl, and aryl;

$R^{20}$ and $R^{21}$ are independently selected from the group consisting of hydrogen, $C_1$-$C_4$ alkyl, $C_1$-$C_4$ haloalkyl, and aryl;

wherein each $R^a$ is independently hydrogen or $C_1$-$C_4$ alkyl;

wherein each $R^b$ and $R^c$ are independently selected from the group consisting of hydrogen, $SO_2R^7$ and $C_1$-$C_4$ alkyl, wherein he $C_1$-$C_4$ alkyl may be optionally substituted with halogen;

wherein each $R^d$ is independently selected from the group consisting of halogen, oxo, $C_1$-$C_4$ alkyl, and $C_1$-$C_4$ alkoxyl, wherein the $C_1$-$C_4$ alkyl and $C_1$-$C_4$ alkoxyl may be optionally substituted with halogen.

One skilled in the art would appreciate that in the above formula (I), all possible combinations or permutations of different substituents are within the scope of the invention. These compounds can be prepared using readily available materials/reagents and known chemical reactions. Based on common knowledge in the art and the teaching in this disclosure, one skilled in the art should be able to prepare and use these compounds without undue experimentation.

The following reaction schemes, Reaction Scheme 1 through Reaction Scheme 14, provide exemplary procedures that can be used to prepare the compounds of Formula (I). However, one skilled in the art would appreciate that these examples are for illustration only and that modifications or variations are possible without departing from the scope of the invention. A quinoxaline compound synthesized in accordance with embodiments of the invention may be purified with any known techniques, such as by flash column chromatography, high performance liquid chromatography, crystallization, or any other suitable methods.

Intermediate I

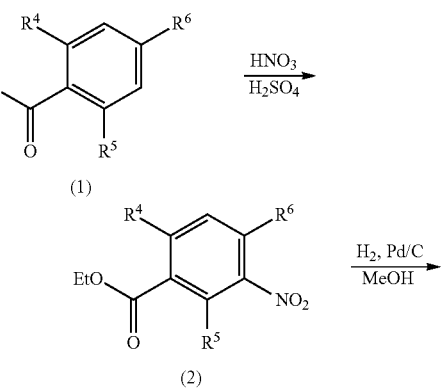

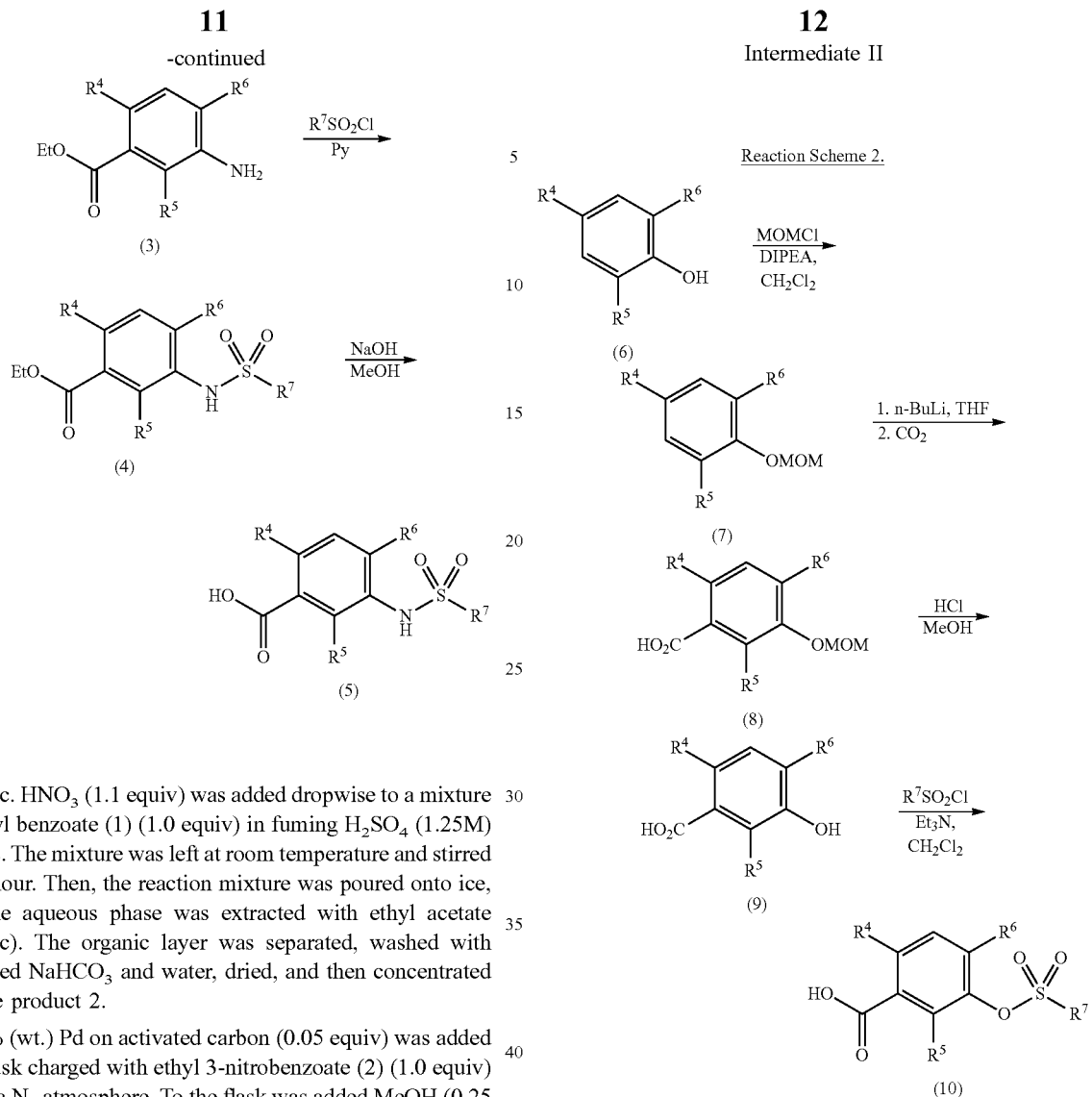

Conc. HNO$_3$ (1.1 equiv) was added dropwise to a mixture of ethyl benzoate (1) (1.0 equiv) in fuming H$_2$SO$_4$ (1.25M) at 0° C. The mixture was left at room temperature and stirred for 1 hour. Then, the reaction mixture was poured onto ice, and the aqueous phase was extracted with ethyl acetate (EtOAc). The organic layer was separated, washed with saturated NaHCO$_3$ and water, dried, and then concentrated to give product 2.

10% (wt.) Pd on activated carbon (0.05 equiv) was added to a flask charged with ethyl 3-nitrobenzoate (2) (1.0 equiv) under a N$_2$ atmosphere. To the flask was added MeOH (0.25 M), and stirred under two H$_2$ balloons overnight. After reaction was complete, the flask was flushed with N$_2$ gas, and the reaction mixture was filtered through celite. The volatiles were removed to afford crude 3-amino ethyl benzoate (3).

Alkyl-1-sulfonyl chloride (1.2 equiv) was slowly added to a solution of 3-amino ethyl benzoate (3) (1.1 equiv) in pyridine (0.5 M) maintained in a cool water bath. The reaction mixture was stirred for 1 hour at room temperature and then poured into cold water. The aqueous phase was extracted with EtOAc. The organic layer was separated, washed with saturated NH$_4$Cl and brine, then dried in MgSO$_4$, filtered, and concentrated to give 3-(N-(alkylsulfonyl) sulfonamido) ethyl benzoate (4).

A 1N aqueous NaOH solution (3.0 equiv) was added to a solution of ethyl 3-(N-alkylsulfonamido)benzoate (4) (1.0 equiv) in 4:1 THF/MeOH (0.2M). The reaction mixture was stirred at room temperature overnight. The majority of the organic solvents were removed in vacuo. 1N HCl was slowly added to the mixture, and the resulting solid was filtered and rinsed with water. The material was washed with Et$_2$O to give 3-alkylsulfonamido benzoic acid (5).

N,N-Diisopropylethylamine (2.0 equiv) and chloromethyl methyl ether (2.0 equiv) were added to a solution of phenol (6) (1.0 equiv) in dry CH$_2$Cl$_2$ under N$_2$ atmosphere at 0° C. The resulting yellow mixture was stirred for 30 min at 0° C. and then left overnight at room temperature. The organic mixture was diluted with aqueous 10% NaOH and extracted with dichloromethane. The organic layers were combined, dried over MgSO$_4$, filtered, and concentrated in vacuo. The crude product was purified on a silica column. Elution with ethyl acetate in hexane afforded the desired product 7.

To a solution of methoxymethoxy benzene (7) (1.0 equiv) in THF (0.35 M) under nitrogen at −70° C. was added a solution of 1.4 M n-butyllithium in hexanes (0.99 equiv) dropwise over 10 min. The mixture was stirred at −70° C. for 1.5 hr and was then decanted onto pulverized dry ice. Once the effervescence had subsided, the mixture was allowed to warm to room temperature (RT) and water was added. The aqueous solution was extracted twice with ether to afford compound 8. Compound 8 was dissolved in methanol and then acidified to pH 1 by the addition of concentrated hydrochloric acid. The resulting suspension was sonicated for 5 min and was then extracted twice with CH$_2$Cl$_2$. The combined CH$_2$Cl$_2$ extracts were dried with MgSO$_4$ and evaporated in vacuo to afford product 9.

Alkyl sulfonyl chloride (1.2 equiv) was slowly added to a solution of 3-hydroxy benzoic acid (9) (1.0 equiv) in triethylamine (0.5 M in CH$_2$Cl$_2$) maintained in a cool water bath. The reaction mixture was stirred for 1 hour at room temperature. Water was added and the organic layer was separated, washed with water and brine, then dried with MgSO$_4$, filtered and concentrated to afford product 10.

Intermediate III

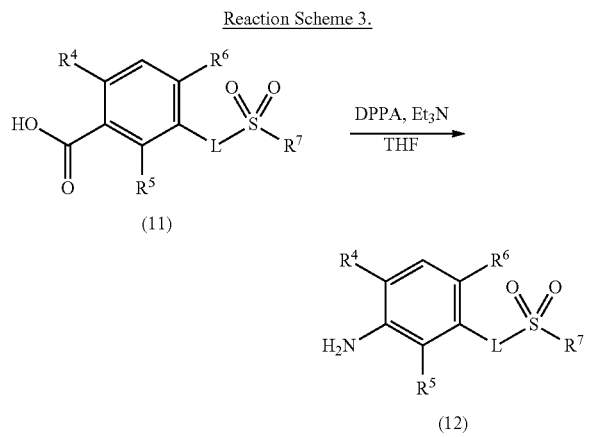

To a solution of benzoic acid (11) (1 equiv) in THF (0.25 M) was added triethylamine (2.3 equiv) and diphenylphosphonic azide (DPPA) (1.15 equiv). The reaction mixture was stirred at room temperature for 3 hours and then warmed to 80° C. for 2 hours. Water was added, and the mixture stirred at 80° C. for 15 hours. The reaction mixture was diluted with EtOAc, and the organic layer was washed with saturated aq. NaHCO$_3$ solution and brine. The solvent was removed under reduced pressure and the residual purified via silica gel column chromatography to give compound 12.

Intermediate IV

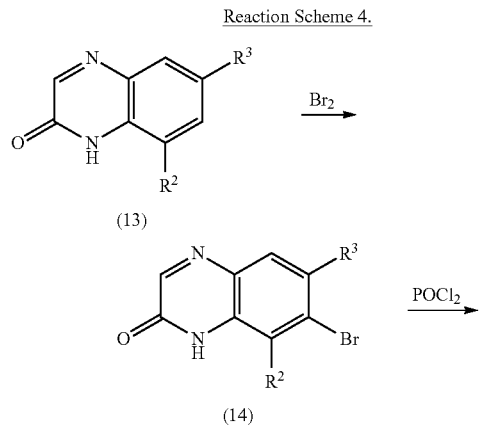

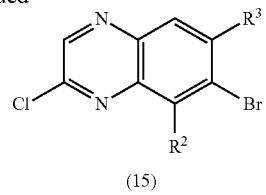

Bromine (1.0 equiv) was slowly added to a solution of substituted-quinoxalinone (20) in acetic acid (0.1M). The reaction mixture was stirred at ambient temperature for 1.5 hours. The resulting solids were collected by filtration and washed with hexanes to afford 7-bromo-substituted-quinoxalinone (14).

A suspension of 7-bromo-substituted-quinoxalinone (14) (1.0 equiv) in POCl$_3$ (1.0 M) was heated to reflux for 6 hours. The resulting clear solution was then cooled to room temperature and quenched by water. The resulting solids were collected by filtration to afford 7-bromo-2-chloro-substituted-quinoxaline (15), which was carried to the next step without further purification.

Intermediate V

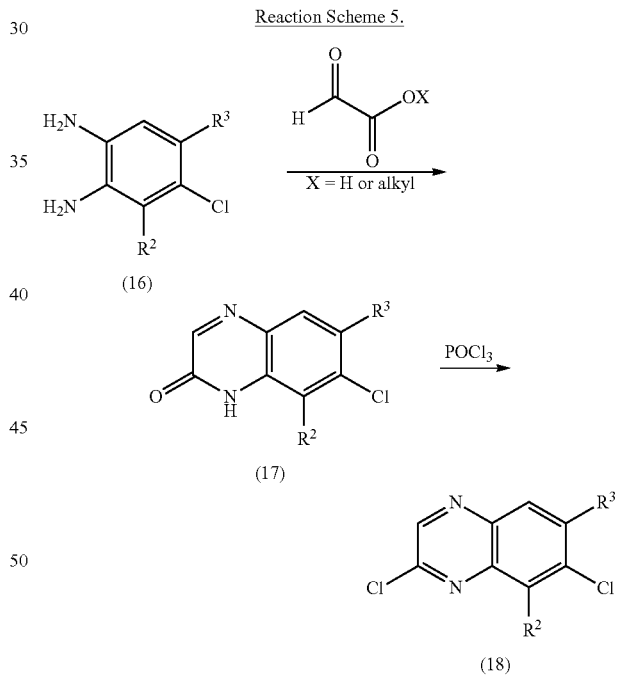

Glyoxylic acid or alkyl glyoxalate and substituted-4-chlorobenzene-1,2-diamine (16) were stirred in organic solvent for 6 hours. The resulting products were purified to afford 7-chloro-substituted-quinoxalinone (17).

A suspension of 7-chloro-substituted-quinoxalinone (17) (1.0 equiv) in POCl$_3$ (1.0 M) was heated to reflux for 6 hours. The resulting clear solution was then cooled to room temperature and quenched by water. The resulting solids were collected by filtration to afford 2,7-dichloro-substituted-quinoxaline (18), which was carried to the next step without further purification.

Intermediate VI

Reaction Scheme 6.

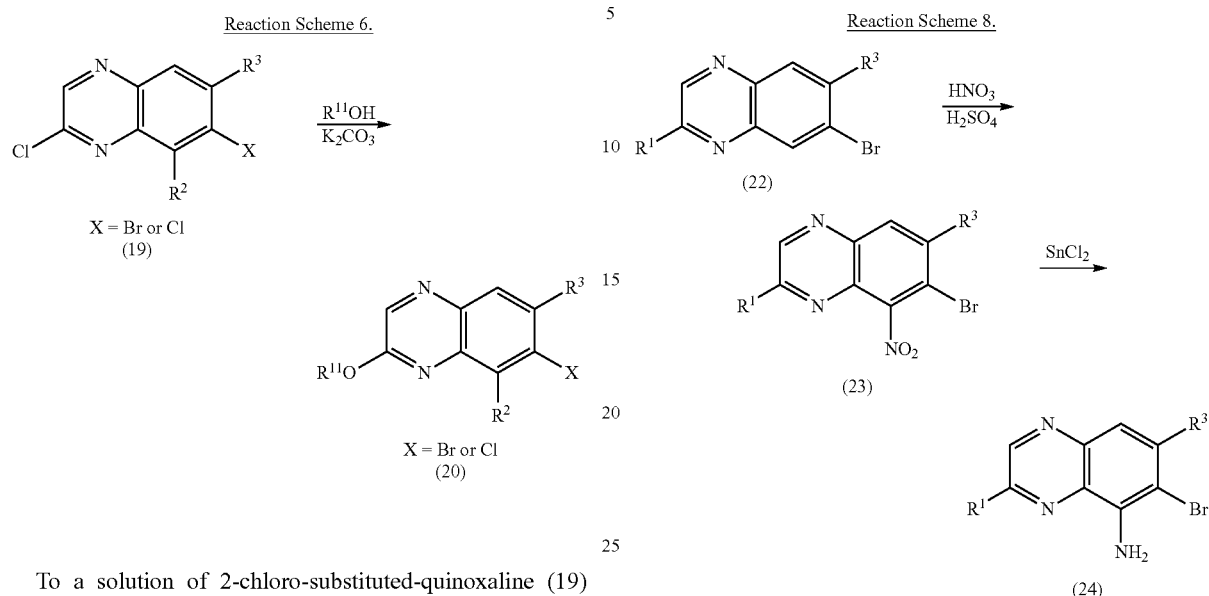

To a solution of 2-chloro-substituted-quinoxaline (19) (1.0 equiv) in $R^{13}OH$ (0.5 M) was added potassium carbonate (1.1 equiv) at room temperature and the reaction was heated at 40° C. for 2 hours. After cooling, the reaction mixture was filtered and concentrated in vacuo. The resulting residue was diluted with ethyl acetate, washed with brine, dried over $MgSO_4$ and concentrated in vacuo to afford compound 20.

Intermediate VII

Reaction Scheme 7.

To a solution of 2-chloro-substituted-quinoxaline (19) (1.0 equiv) in $R^{11}R^{12}NH$ (0.5 M) was added triethylamine (1.1 equiv) at room temperature and the reaction was heated at 60° C. for 2 hours. After cooling, the reaction mixture was filtered and concentrated in vacuo. The resulting residue was diluted with ethyl acetate, washed with brine, dried over $MgSO_4$ and concentrated in vacuo to afford compound 21.

Intermediate VIII

Reaction Scheme 8.

To a solution of 7-bromo-substituted-quinoxaline (22) (1.0 equiv) in sulfuric acid was added nitric acid. The reaction mixture was stirred at room temperature for 8 hours. The mixture was poured onto an ice-$H_2O$ mixture, and filtered. The solid was washed with ethyl acetate to afford the 7-bromo-8-nitro-substituted-quinoxaline (23).

To a solution of 7-bromo-8-nitro-substituted-quinoxaline (23) (1.0 equiv) in ethyl acetate/dimethylformamide (6:1) was added tin (II) chloride ($SnCl_2$; 10.0 equiv). The reaction mixture was stirred at 100° C. for 16 hours. After cooling, the reaction mixture was concentrated in vacuo. The resulting residue was diluted with ethyl acetate, washed with saturated aq. $NaHCO_3$ solution and brine, dried over $MgSO_4$, filtered and concentrated in vacuo to afford 6-bromo-substituted-quinoxalin-5-amine (24).

Intermediate IX

Reaction Scheme 9.

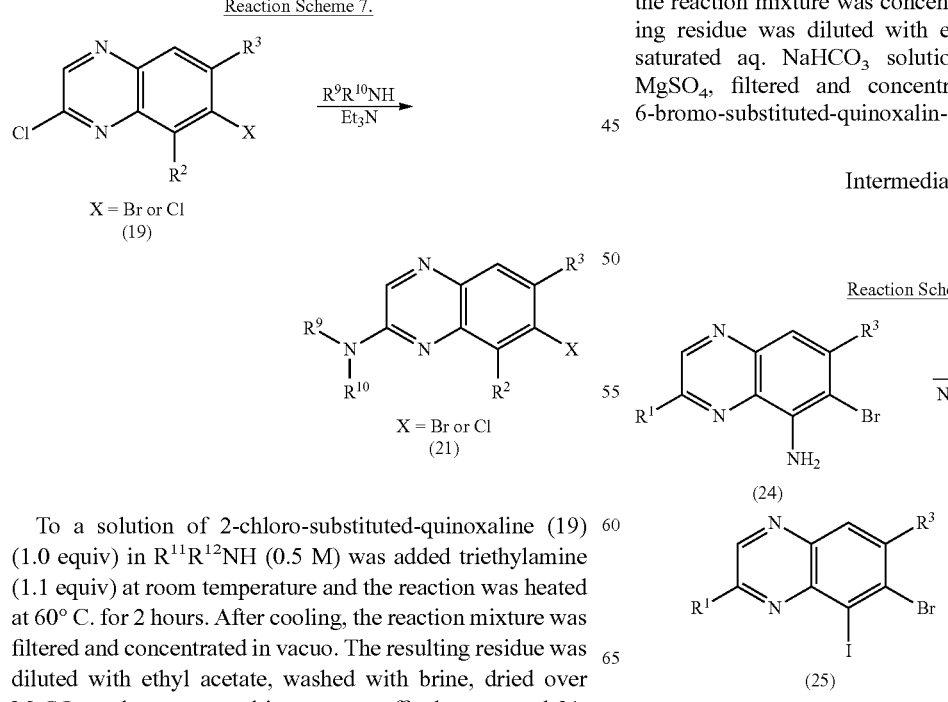

-continued

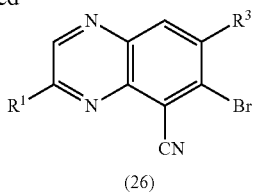

(26)

7-Bromo-substituted-quinoxalin-5-amine (24) (1.0 equiv), hydrogen chloride (1.5 equiv) and sodium nitrite (1.1 equiv) in H$_2$O were added potassium iodide (1.2 equiv) at −10° C. The reaction was stirred at room temperature for 16 hours. The crude reaction mixture was diluted with EtOAc, and the organic layer was washed with brine, dried over MgSO$_4$ and filtered. The solvent was removed under reduced pressure and the residual purified via silica gel column chromatography to give 7-bromo-8-iodo-substituted-quinoxaline (25).

7-Bromo-8-iodo-substituted-quinoxaline (25) (1.0 equiv), potassium cyanide (2.0 equiv), copper iodide (1.1 equiv) and 1,10-phenanthroline monohydrate (0.2 equiv) in dimethylformamide were heated at 110° C. for 24 hours in sealed tube. The reaction mixture was filtered and washed with methanol, and the solvent was removed under vacuo. The crude reaction mixture was diluted with EtOAc, and the organic layer was washed with saturated aq. NaHCO$_3$ solution and brine, dried over MgSO$_4$ and filtered. Ethyl acetate was removed under reduced pressure and the residual purified via silica gel column chromatography to give 7-bromo-8-cyano-substituted-quinoxaline (26).

Final Product I

Reaction Scheme 10.

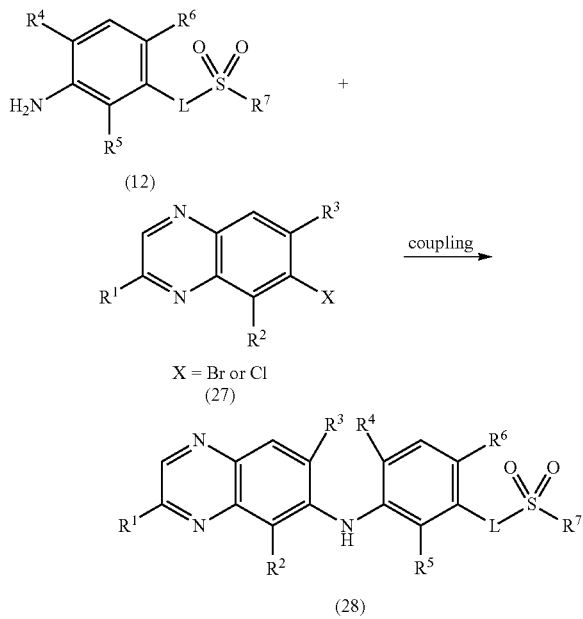

Substituted-quinoxalinone (27) (1.0 equiv), cesium carbonate (3.0 equiv), Pd(OAc)$_2$ (0.1 equiv) compound 12 (1.0 equiv) and xantphos (0.02 equiv; 4,5-Bis(diphenylphosphino)-9,9-dimethylxanthene) in dioxane (0.3 M) were heated at 110° C. for 2 hours. The solution was filtered, washed with methanol and concentrated in vacuo. The residual was purified via silica gel column chromatography to give quinoxaline compound 28.

The above reaction schemes illustrate how quinoxaline compounds of the invention may be prepared. One skilled in the art would appreciate that the reactions involved and the reagents used in these reactions are known in the art. Therefore, based on the above teachings and the common knowledge in the art, quinoxaline compounds with various substituents, as defined herein, can be prepared by one skilled in the art without inventive efforts.

The quinoxaline compounds mentioned herein may contain a non-aromatic double bond and one or more asymmetric centers, e.g., in the substituents attached to the core aromatic rings. Therefore, these compounds may occur as racemates and racemic mixtures, single enantiomers, individual diastereomers, diastereomeric mixtures, and cis- or trans-isomeric forms. All such isomeric forms are within the scope of the invention. The quinoxaline compounds of the invention may have acidic or basic functional groups (e.g., on the substitution groups) that may form salts, particularly pharmaceutically acceptable salts. Formation of such salts is a routine practice in the pharmaceutical industry. Examples of salts that may be used with quinoxaline compounds of the invention, for example, include hydrochloride, sulfate, formate, acetate, malate, succinate, etc. for the basic functional groups, and hydroxide, ammonium, alkylammonium, etc. for acidic functional groups. Such quinoxaline salts are within the scope of the invention. Similarly, the acidic or basic groups may be functionalized, for example into esters. Such functionalized derivatives will be hydrolyzed in vivo. Therefore, such derivatives may function as pro-drugs of the quinoxaline compounds of the invention. Formation of pro-drugs involves only routine skills and one skilled in the art would know how to prepare and use such pro-drugs without undue experimentation.

Also within the scope of this invention are (1) a pharmaceutical composition that contains an effective amount of at least one of the quinoxaline compounds of this invention and a pharmaceutically acceptable carrier, (2) a method for treating a protein kinase-related disease (e.g., cancer) by administering to a subject in need of such treatment an effective amount of such a quinoxaline compound, and (3) a method of decreasing the activity of at least one protein kinase by contacting the at least one protein kinase with at least one of the quinoxaline compounds of this invention.

As used herein, the term a "protein kinase-related disease/disorder," or "protein kinase-associated disease/disorder," or "disease/disorder modulated by a protein kinase" refers to a disease or condition that is characterized by abnormal a protein kinase (PK) activity or a disease or condition that can be treated with changes to the activity of at least one PK. Abnormal PK activity can arise as the result of elevated PK expression level, or presence of PK expression that does not happen in normal conditions. PK-related disease/disorder described herein include, but not limited to, cancer, diabetes, a hyper-proliferation disorder, hyperproliferative disorders of the kidney, renal disease, von Hippel-Lindau disease, restenosis, fibrosis, psoriasis, osteoarthritis, rheumatoid arthritis, an inflammatory disorder, immunological disorders such as autoimmune diseases (e.g., AIDS, lupus, etc.), cardiovascular disorders (e.g. atherosclerosis), and blood vessel proliferative disorders such as abnormal vasculogenesis.

The term "treating" refers to administering a quinoxaline compound to a subject that has a protein kinase-related disease/disorder, or has a symptom of or a predisposition toward it, with the purpose to alleviate, relieve, alter, remedy, ameliorate, improve, affect or reduce the risk of the disorder, the symptoms of or the predisposition toward the disorder. For example, treating cancer refers to the treatment results in inhibition of cancer growth or cancer cell growth, regression in cancer growth (i.e. it reduces the size of a detectable cancer), or the disappearance of a cancer.

The term "an effective amount" refers to the amount of the active agent that is required to confer the intended therapeutic effect in the subject. Effective amounts may vary, as recognized by those skilled in the art, depending on routes of administration, excipient usages, and the possibility of co-usage with other agents. Determination of an effective amount requires only routine skills, and one skilled in the art would be able to determine such effective amounts for the intended use without undue experimentation. The subject in need of the treatment can be a mammal. The term "mammal" refers to human or nonhuman mammal, for example, dogs, cats, pigs, cows, sheep, goats, horses, rats, or mice.

Cancer that can be treated by the methods of the invention includes any abnormal cell or tissue growth, for example, a tumor, whether malignant, pre-malignant, or non-malignant. Cancer is characterized by uncontrolled proliferation of cells that may or may not invade the surrounding tissue and, hence, may or may not metastasize to new body sites. Cancer encompasses carcinomas, which are cancers of epithelial cells; carcinomas include squamous cell carcinomas, adenocarcinomas, melanomas, and hepatomas. Cancer also encompasses sarcomas, which are tumors of mesenchymal origin; sarcomas include osteogenic sarcomas, leukemias, and lymphomas. Cancers may involve one or more neoplastic cell type. The term cancer includes, as non-limiting examples, lung cancer, colon cancer, colorectal cancer, breast cancer, prostate cancer, liver cancer, pancreatic cancer, bladder cancer, gastric cancer, renal cancer, salivary gland cancer, ovarian cancer, uterine body cancer, cervical cancer, oral cancer, skin cancer, brain cancer, lymphoma, and leukemia. It also includes drug resistant cancer (including but not limited to multidrug resistant cancer).

The compounds described herein can be administered to a mammal in conjunction with radiation therapy, immunotherapy, monoclonal antibody therapy, hormonal therapy, chemotherapy using other agents, and/or surgery. By in conjunction with, the therapies need not occur at the same time, but can be in succession, or alternating with each other and/or periods of rest and recovery.

In accordance with some embodiments of the invention, a protein kinase-related disease/disorder, such as cancer, may be treated with a method comprising administering an effective amount of at least one quinoxaline compound of this invention and at least one chemotherapeutic agent to a mammal. Non-limiting examples of chemotherapeutic agent include, PK inhibitors other than the compound described herein (e.g., imatinib mesylate, gefitinib, dasatinib, erlotinib, lapatinib, sunitinib, nilotinib, and sorafenib; antibodies, including, e.g., trastuzumab, rituximab, cetuximab, and bevacizumab; mitoxantrone; dexamethasone; prednisone; and temozolomide), alkylating agents (e.g., melphalan, chlorambucil, busulfan, thiotepa, ifosfamide, carmustine, lomustine, semustine, streptozocin, decarbazine, and cyclophosphamide), mitotic inhibitors, antimetabolites (e.g., capecitibine, gemcitabine, 5-fluorouracil or 5-fluorouracil/leucovorin, fludarabine, cytarabine, mercaptopurine, thioguanine, pentostatin, and methotrexate), cell cycle inhibitors, enzymes, hormones, anti-hormones, growth-factor inhibitors, plant alkaloids and terpenoids, topoisomerase inhibitors (e.g., etoposide, teniposide, camptothecin, topotecan, irinotecan, doxorubicin, and daunorubicin), antitumor antibiotics (e.g., actinomycin D, bleomycin, mitomycin C, adriamycin, daunorubicin, idarubicin, doxorubicin and pegylated liposomal doxorubicin), vinca alkaloids (e.g., vincristine and vinblastin), taxanes (e.g., paclitaxel and docetaxel), platinum agents (e.g., cisplatin, carboplatin, and oxaliplatin), thalidomide and related analogs (e.g., CC-5013 and CC-4047), monoclonal antibodies, and antiangiogenic agents.

As used herein, the term "contacting" means bringing a compound of this invention and at least one PK together in a way that the compound can decrease the activity of the at least one PK, either directly, i.e., by acting on the protein kinase itself, or indirectly, i.e., by acting on another molecule on which the activity of the at least one PK is dependent. "Contacting" can occur in vitro or in vivo. For instance, in a test tube that contains the at least one PK; in a culture dish that has whole cells grown; or in a mammal to which the compound of this invention is administered. Examples of target PK include, but are not limited to EGFR, CDK1, Aurora A & B kinase, MAP, CDK2, Raf, NEK (including NEK 4a, NEK 4b, NEK 5 and NEK 6), BUB1, VEGFR, C-MET, HER2, HER3, HER4, IR, IGF-IR, IRR, PDGFRct, PDGFRO, CSFIR, C-Kit, C-fms, Flk-1 R, Flk4, KDRlFlk-1, FLT-1, FLT3, FGFR-1, FGFR-2, FGFR-3, FGFR4, Src, Frk, Btk, Csk, Abl, ZAP70, Fes, Fps, Fak, Jak, Ack, Yes, Fyn, Lyn, Lck, Blk, Hck, Fgr, Aur2, and Yrk.

To practice a method of this invention, the above-described pharmaceutical composition can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In accordance with some embodiments of the invention, a quinoxaline compound of this invention may be administered intravenously, suitable carriers may include, but are not limited to, physiological saline or phosphate buffered saline (PBS), and solutions containing thickening and solubilizing agents, such as glucose, polyethylene glycol, and polypropylene glycol and mixtures thereof.

A sterile injectable composition, e.g., a sterile injectable aqueous or oleaginous suspension, can be formulated according to techniques known in the art using suitable dispersing or wetting agents (such as TWEEN 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectable, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well known in the art of pharmaceutical formulation. A quinoxaline compound-containing composition can also be administered in the form of suppositories for rectal administration.

A carrier in the pharmaceutical composition should be "acceptable" in the sense of being compatible with the active ingredient of the formulation (and preferably, capable of stabilizing it) and not deleterious to the subject to be treated. One or more solubilizing agents (e.g., cyclodextrin) which form more soluble complexes with the active quinoxaline compounds can be utilized as pharmaceutical carriers for delivery of the active compounds. Examples of other carriers include colloidal silicon dioxide, magnesium stearate and sodium lauryl sulfate.

Suitable in vitro assays can be used to preliminarily evaluate the efficacy of the quinoxaline compounds of this invention in anticancer activities such as inhibiting growth of tumor cells. The compounds can further be examined for their efficacy in treating cancer. For example, a compound can be administered to an animal (e.g., a mouse model) having cancer and its therapeutic effects are then assessed. Based on the results, an appropriate dosage range and administration route can also be determined.

Without further elaboration, it is believed that the above description has adequately enabled the present invention. The following examples are, therefore, to be construed as merely illustrative, and not limitative of the remainder of the disclosure in any way whatsoever.

EXAMPLES

Exemplary quinoxaline compounds are listed in Table 1. Their calculated mass and observed ESI-MS data are provided in Table 2.

TABLE 1

Quinoxaline compounds

| Cpd. ID | Structure |
|---|---|
| 1 | N1-3-[(3-{2,6-difluoro-3-[(propylsulfonyl)amino]anilino}-6-quinoxalinyl)amino]-2,4-difluorophenyl]-1 propanesulfonamide |
| 2 | N1-(3-{[3-(2,6-difluoroanilino)-6-quinoxalinyl]amino}-2,4-difluorophenyl)-1-propanesulfonamide |
| 3 | N1-{3-[(5-amino-3-methoxy-6-quinoxalinyl)amino]-2,4-difluorophenyl}-1-propanesulfonamide |
| 4 | N1-{2,4-difluoro-3-[(3-methoxy-5-nitro-6-quinoxalinyl)amino]phenyl}-1-propanesulfonamide |

TABLE 1-continued

Quinoxaline compounds

| Cpd. ID | Structure |
|---|---|
| 5 | 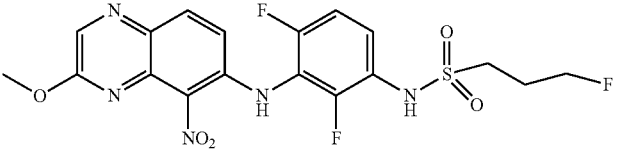 [SMILES: COc1cnc2ccc(Nc3c(F)ccc(NS(=O)(=O)CCCF)c3F)c([N+](=O)[O-])c2n1]
N1-{2,4-difluoro-3-[(3-methoxy-5-nitro-6-quinoxalinyl)amino]phenyl}-3-fluoro-1-propanesulfonamide |
| 6 | 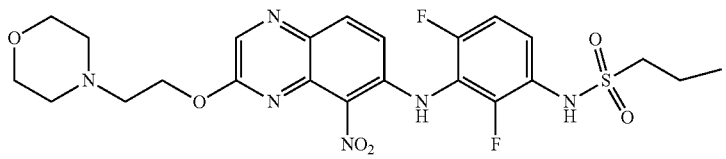 [SMILES: CCCS(=O)(=O)Nc1ccc(F)c(Nc2ccc3ncc(OCCN4CCOCC4)nc3c2[N+](=O)[O-])c1F]
N1-(2,4-difluoro-3-{[3-(2-morpholinoethoxy)-5-nitro-6-quinoxalinyl]amino}phenyl)-1-propanesulfonamide |
| 7 | 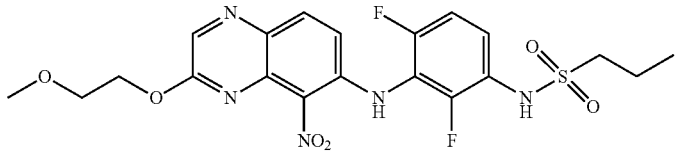 [SMILES: CCCS(=O)(=O)Nc1ccc(F)c(Nc2ccc3ncc(OCCOC)nc3c2[N+](=O)[O-])c1F]
N1-(2,4-difluoro-3-[3-(2-methoxyethoxy)-5-nitro-6-quinoxalinyl]aminophenyl)-1-propanesulfonamide |
| 8 | 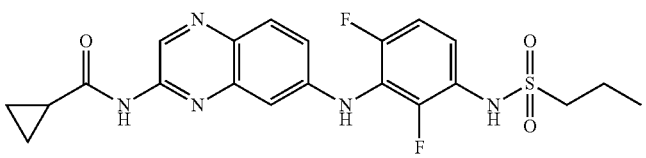 [SMILES: CCCS(=O)(=O)Nc1ccc(F)c(Nc2ccc3ncc(NC(=O)C4CC4)nc3c2)c1F]
N1-(7-{2,6-difluoro-3-[(propylsulfonyl)amino]anilino}-2-quinoxalinyl)-1-cyclopropanecarboxamide |
| 9 | 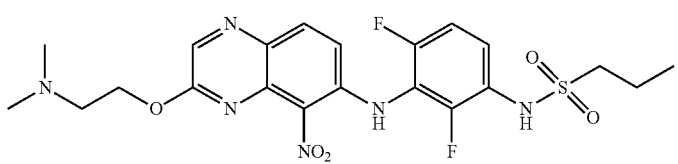 [SMILES: CCCS(=O)(=O)Nc1ccc(F)c(Nc2ccc3ncc(OCCN(C)C)nc3c2[N+](=O)[O-])c1F]
N1-[3-({3-[2-(dimethylamino)ethoxy]-5-nitro-6-quinoxalinyl}amino)-2,4-difluorophenyl]-1-propanesulfonamide |
| 10 | 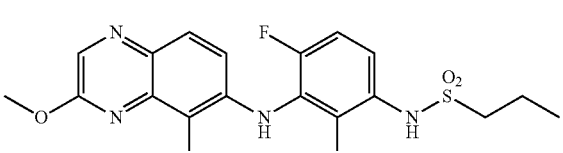
N1-{3-[(5-cyano-3-methoxy-6-quinoxalinyl)amino]-2,4-difluorophenyl}-1-propanesulfonamide |

TABLE 1-continued

Quinoxaline compounds

| Cpd. ID | Structure |
|---|---|
| 11 | 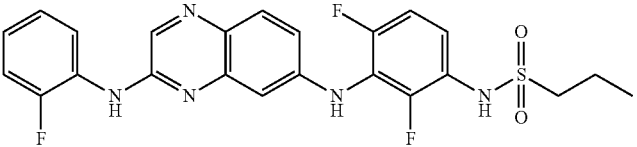 [SMILES: CCCS(=O)(=O)Nc1ccc(F)c(Nc2ccc3ncc(Nc4ccccc4F)nc3c2)c1F]<br>N1-(2,4-difluoro-3-{[3-(2-fluoroanilino)-6-quinoxalinyl]amino}phenyl)-1-propanesulfonamide |
| 12 | 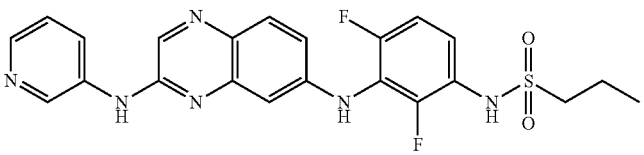 [SMILES: CCCS(=O)(=O)Nc1ccc(F)c(Nc2ccc3ncc(Nc4cccnc4)nc3c2)c1F]<br>N1-(2,4-difluoro-3-{[3-(3-pyridylamino)-6-quinoxalinyl]amino}phenyl)-1-propanesulfonamide |
| 13 | 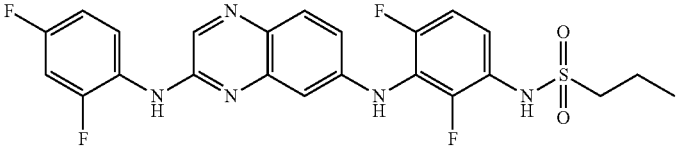 [SMILES: CCCS(=O)(=O)Nc1ccc(F)c(Nc2ccc3ncc(Nc4ccc(F)cc4F)nc3c2)c1F]<br>N1-(3-{[3-(2,4-difluoroanilino)-6-quinoxalinyl]amino}-2,4-difluorophenyl)-1-propanesulfonamide |
| 14 | 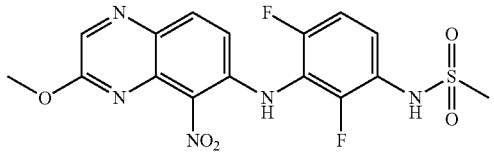<br>N-{2,4-difluoro-3-[(3-methoxy-5-nitro-6-quinoxalinyl)amino]phenyl}methanesulfonamide |
| 15 | 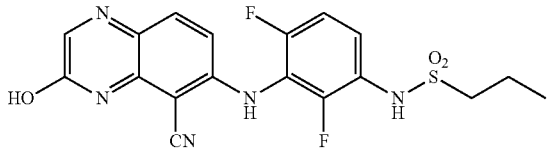 [SMILES: CCCS(=O)(=O)Nc1ccc(F)c(Nc2ccc3ncc(O)nc3c2C#N)c1F]<br>N1-{3-[(5-cyano-3-hydroxy-6-quinoxalinyl)amino]-2,4-difluorophenyl}-1-propanesulfonamide |
| 16 | 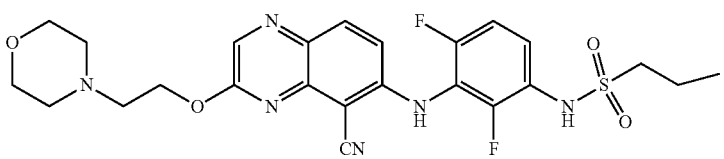 [SMILES: CCCS(=O)(=O)Nc1ccc(F)c(Nc2ccc3ncc(OCCN4CCOCC4)nc3c2C#N)c1F]<br>N1-(3-{[5-cyano-3-(2-morpholinoethoxy)-6-quinoxalinyl]amino}-2,4-difluorophenyl)-1-propanesulfonamide |

TABLE 1-continued

Quinoxaline compounds

| Cpd. ID | Structure |
|---|---|
| 17 | 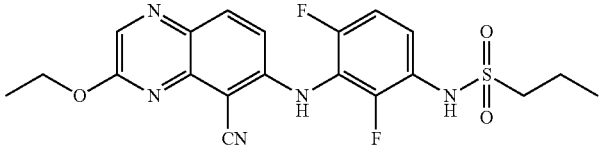 [SMILES: CCCS(=O)(=O)Nc1ccc(F)c(Nc2ccc3ncc(OCC)nc3c2C#N)c1F]

N-(3-(5-cyano-3-ethoxyquinoxalin-6-ylamino)-2,4-difluorophenyl)propane-1-sulfonamide |
| 18 | 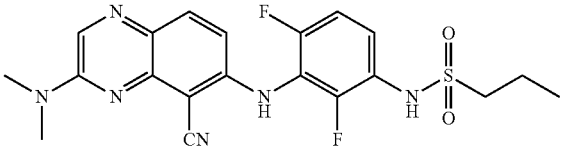 [SMILES: CCCS(=O)(=O)Nc1ccc(F)c(Nc2ccc3ncc(N(C)C)nc3c2C#N)c1F]

N-(3-(5-cyano-3-(dimethylamino)quinoxalin-6-ylamino)-2,4-difluorophenyl)propane-1-sulfonamide |
| 19 | 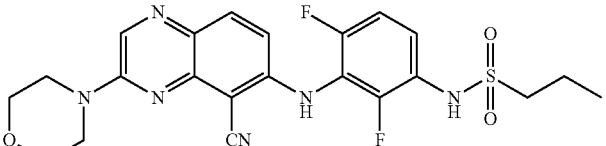

N-(3-(5-cyano-3-morpholinoquinoxalin-6-ylamino)-2,4-difluorophenyl)propane-1-sulfonamide |
| 20 | 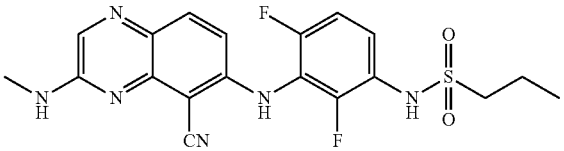

N-(3-(5-cyano-3-(methylamino)quinoxalin-6-ylamino)-2,4-difluorophenyl)propane-1-sulfonamide |
| 21 | 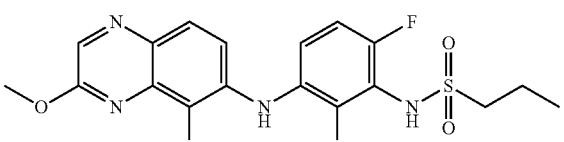

N-(3-(5-cyano-3-methoxyquinoxalin-6-ylamino)-2,6-difluorophenyl)propane-1-sulfonamide |
| 22 | 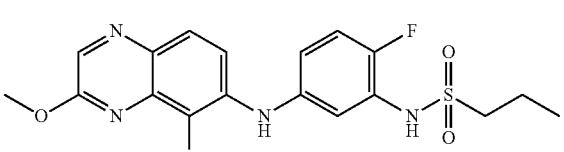

N-(5-(5-cyano-3-methoxyquinoxalin-6-ylamino)-2-fluorophenyl)propane-1-sulfonamide |

TABLE 1-continued

Quinoxaline compounds

| Cpd. ID | Structure |
|---|---|
| 23 | N-(3-(5-cyano-3-morpholinoquinoxalin-6-ylamino)-4-fluorophenyl)propane-1-sulfonamide |
| 24 | N-(3-(5-cyano-3-ethoxyquinoxalin-6-ylamino)-4-fluorophenyl)benzenesulfonamide |
| 25 | N-(3-(5-cyano-3-morpholinoquinoxalin-6-ylamino)-4-fluorophenyl)benzenesulfonamide |
| 26 | N-(3-(5-cyano-3-morpholinoquinoxalin-6-ylamino)-4-fluorophenyl)methanesulfonamide |
| 27 | N-(3-(5-cyano-3-ethoxyquinoxalin-6-ylamino)-4-fluorophenyl)methanesulfonamide |
| 28 | N-(3-(5-cyano-3-(dimethylamino)quinoxalin-6-ylamino)-4-fluorophenyl)propane-1-sulfonamide |

TABLE 1-continued

Quinoxaline compounds

| Cpd. ID | Structure |
|---|---|
| 29 | 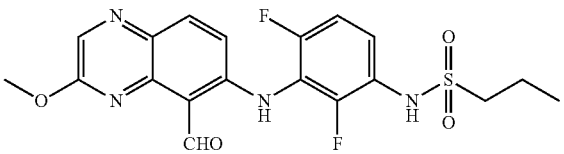 [SMILES: CCCS(=O)(=O)Nc1ccc(F)c(Nc2ccc3ncc(OC)nc3c2C=O)c1F]<br>N-(2,4-difluoro-3-(5-formyl-3-methoxyquinoxalin-6-ylamino)phenyl)propane-1-sulfonamide |
| 30 | 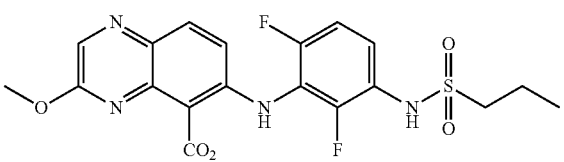<br>6-(2,6-difluoro-3-(propylsulfonamido)phenylamino)-3-methoxyquinoxaline-5-carboxylic acid |
| 31 | 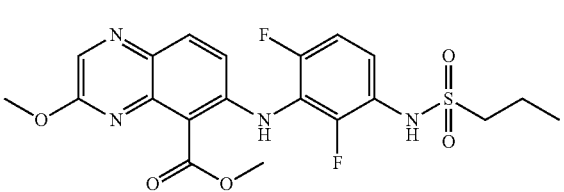 [SMILES: CCCS(=O)(=O)Nc1ccc(F)c(Nc2ccc3ncc(OC)nc3c2C(=O)OC)c1F]<br>methyl 6-(2,6-difluoro-3-(propylsulfonamido)phenylamino)-3-methoxyquinoxaline-5-carboxylate |
| 32 | 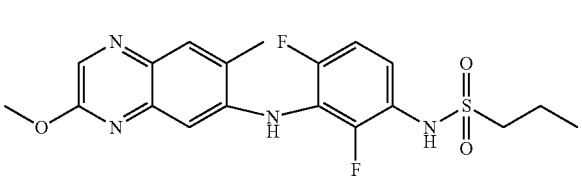 [SMILES: CCCS(=O)(=O)Nc1ccc(F)c(Nc2cc3nc(OC)cnc3cc2C)c1F]<br>N-(2,4-difluoro-3-(3-methoxy-7-methylquinoxalin-6-ylamino)phenyl)propane-1-sulfonamide |
| 33 | 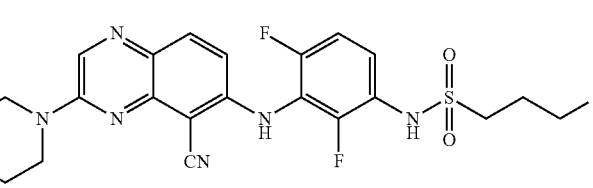<br>N-(3-(5-cyano-3-morpholinoquinoxalin-6-ylamino)-2,4-difluorophenyl)-3-fluoropropane-1-sulfonamide |
| 34 | 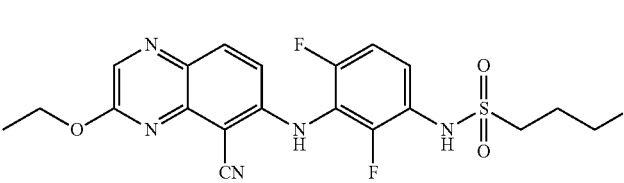<br>N-(3-(5-cyano-3-ethoxyquinoxalin-6-ylamino)-2,4-difluorophenyl)-3-fluoropropane-1-sulfonamide |

TABLE 1-continued

Quinoxaline compounds

| Cpd. ID | Structure |
|---|---|
| 35 | 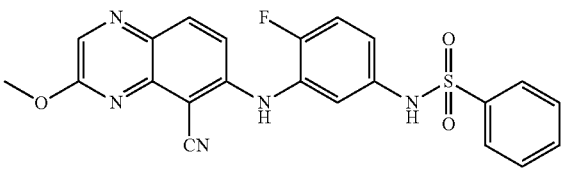 [SMILES: COc1cnc2ccc(Nc3cc(NS(=O)(=O)c4ccccc4)ccc3F)c(C#N)c2n1]<br>N-(3-(5-cyano-3-methoxyquinoxalin-6-ylamino)-4-fluorophenyl)benzenesulfonamide |
| 36 | 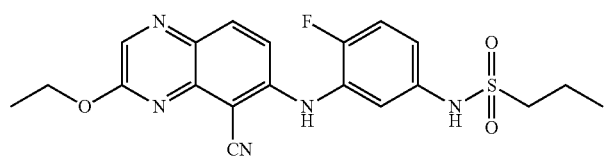 [SMILES: CCCS(=O)(=O)Nc1ccc(F)c(Nc2ccc3ncc(OCC)nc3c2C#N)c1]<br>N-(3-(5-cyano-3-ethoxyquinoxalin-6-ylamino)-4-fluorophenyl)propane-1-sulfonamide |
| 37 | 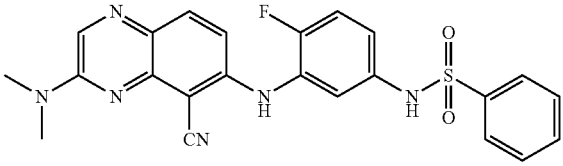 [SMILES: CN(C)c1cnc2ccc(Nc3cc(NS(=O)(=O)c4ccccc4)ccc3F)c(C#N)c2n1]<br>N-(3-(5-cyano-3-(dimethylamino)quinoxalin-6-ylamino)-4-fluorophenyl)benzenesulfonamide |
| 38 | 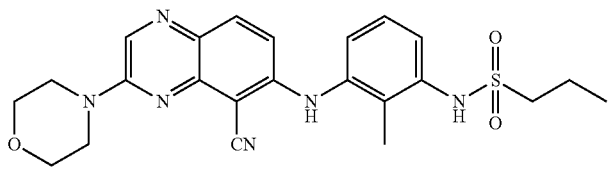 [SMILES: CCCS(=O)(=O)Nc1cccc(Nc2ccc3ncc(N4CCOCC4)nc3c2C#N)c1C]<br>N-(3-(5-cyano-3-morpholinoquinoxalin-6-ylamino)-2-methylphenyl)propane-1-sulfonamide |
| 39 | 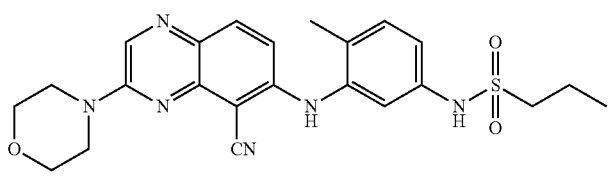 [SMILES: CCCS(=O)(=O)Nc1ccc(C)c(Nc2ccc3ncc(N4CCOCC4)nc3c2C#N)c1]<br>N-(3-(5-cyano-3-morpholinoquinoxalin-6-ylamino)-4-methylphenyl)propane-1-sulfonamide |
| 40 | 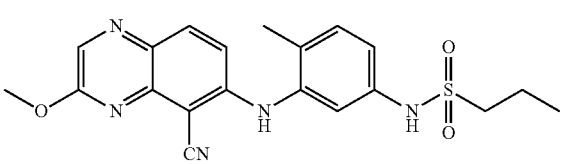 [SMILES: CCCS(=O)(=O)Nc1ccc(C)c(Nc2ccc3ncc(OC)nc3c2C#N)c1]<br>N-(3-(5-cyano-3-methoxyquinoxalin-6-ylamino)-4-methylphenyl)propane-1-sulfonamide |

TABLE 1-continued

Quinoxaline compounds

| Cpd. ID | Structure |
|---|---|
| 41 | N-(3-(5-cyano-3-methoxyquinoxalin-6-ylamino)-4-fluorophenyl)methanesulfonamide |
| 42 | N-(3-(5-cyano-3-methoxyquinoxalin-6-ylamino)-2,4-difluorophenyl)-N-ethylpropane-1-sulfonamide |
| 43 | N-(3-(5-cyano-3-methoxyquinoxalin-6-ylamino)-2,4-difluorophenyl)-N-methylpropane-1-sulfonamide |
| 44 | N-(3-(5-cyano-3-methoxyquinoxalin-6-ylamino)-2-methylphenyl)propane-1-sulfonamide |
| 45 | N-(5-(5-cyano-3-methoxyquinoxalin-6-ylamino)-2-methylphenyl)propane-1-sulfonamide |
| 46 | N-(2-chloro-3-(5-cyano-3-methoxyquinoxalin-6-ylamino)-4-fluorophenyl)propane-1-sulfonamide |

TABLE 1-continued

Quinoxaline compounds

| Cpd. ID | Structure |
|---|---|
| 47 | N-(2-chloro-3-(5-cyano-3-methoxyquinoxalin-6-ylamino)-4-fluorophenyl)benzenesulfonamide |
| 48 | N-(2-chloro-3-(5-cyano-3-morpholinoquinoxalin-6-ylamino)-4-fluorophenyl)propane-1-sulfonamide |
| 49 | N-(2-chloro-3-(5-cyano-3-morpholinoquinoxalin-6-ylamino)-4-fluorophenyl)benzenesulfonamide |
| 50 | N-(2-cyano-3-(5-cyano-3-methoxyquinoxalin-6-ylamino)phenyl)propane-1-sulfonamide |

TABLE 2 calculated mass and observed ESI-MS data

| Cpd. ID | Calculated Mass | Observed ESI-MS |
|---|---|---|
| 1 | 626.14 | 627.4 (M + H)⁺ |
| 2 | 505.12 | 506.2 (M + H)⁺ |
| 3 | 423.12 | 424.0 (M + H)⁺ |
| 4 | 453.09 | 454.0 (M + H)⁺ |
| 5 | 471.08 | 472.1 (M + H)⁺ |
| 6 | 552.16 | 553.2 (M + H)⁺ |
| 7 | 497.12 | 498.0 (M + H)⁺ |
| 8 | 461.13 | 462.1 (M + H)⁺ |
| 9 | 510.15 | 511.1 (M + H)⁺ |
| 10 | 433.10 | 434.1 (M + H)⁺ |
| 11 | 487.13 | 488.0 (M + H)⁺ |
| 12 | 470.13 | 471.0 (M + H)⁺ |
| 13 | 505.12 | 506.2 (M + H)⁺ |
| 14 | 425.06 | 425.9 (M + H)⁺ |
| 15 | 419.09 | 420.2 (M + H)⁺ |
| 16 | 532.17 | 533.2 (M + H)⁺ |
| 17 | 447.12 | 448.37 (M + H)⁺ |
| 18 | 446.13 | 447.23 (M + H)⁺ |
| 19 | 488.14 | 489.17 (M + H)⁺ |
| 20 | 432.12 | 432.1 (M + H)⁺ |
| 21 | 433.10 | 434.13 (M + H)⁺ |
| 22 | 415.11 | 416.21 (M + H)⁺ |
| 23 | 470.15 | 471.15 (M + H)⁺ |
| 24 | 436.11 | 464.25 (M + H)⁺ |
| 25 | 504.14 | 505.51 (M + H)⁺ |
| 26 | 422.12 | 443.09 (M + H)⁺ |
| 27 | 401.10 | 402.05 (M + H)⁺ |
| 28 | 428.14 | 429.12 (M + H)⁺ |
| 29 | 436.10 | 437.33 (M + H)⁺ |
| 30 | 452.10 | 453.09 (M + H)⁺ |
| 31 | 466.11 | 467.13 (M + H)⁺ |
| 32 | 422.12 | 423.38 (M + H)⁺ |
| 33 | 506.13 | 507.21 (M + H)⁺ |
| 34 | 465.11 | 466.13 (M + H)⁺ |
| 35 | 449.10 | 450.40 (M + H)⁺ |
| 36 | 429.13 | 430.11 (M + H)⁺ |
| 37 | 462.13 | 463.30 (M + H)⁺ |
| 38 | 466.18 | 467.26 (M + H)⁺ |
| 39 | 466.18 | 467.29 (M + H)⁺ |
| 40 | 411.14 | 412.28 (M + H)⁺ |

TABLE 2-continued calculated mass and observed ESI-MS data

| Cpd. ID | Calculated Mass | Observed ESI-MS |
|---|---|---|
| 41 | 387.08 | 388.21 (M + H)+ |
| 42 | 461.13 | 462.21 (M + H)+ |
| 43 | 447.12 | 448.52 (M + H)+ |
| 44 | 411.14 | 412.18 (M + H)+ |
| 45 | 411.14 | 412.33 (M + H)+ |
| 46 | 449.89 | 450.34 (M + H)+ |
| 47 | 483.90 | 484.18 (M + H)+ |
| 48 | 504.96 | 505.38 (M + H)+ |
| 49 | 538.98 | 539.17 (M + H)+ |
| 50 | 422.12 | 423.42 (M + H)+ |

BIOLOGICAL ACTIVITY

Biological Activity

Various compounds of formula I were tested for their abilities to inhibit a variety of protein kinases. Brief descriptions of different assays are described below.

1. B-Raf Kinase Assay

Inhibition of kinase activity by a test compound disclosed herein was estimated by quantifying the amount of [$^{33}$P] incorporation of a substrate in the presence of the test compound. Standard assay conditions were 5 ng of recombinant B-Raf kinase (Upstate Biotechnology) with 500 ng MEK1(Map-erk kinase; K97R) in the assay buffer (8 μM ATP, 0.5 μCi [$^{33}$P]ATP (specific activity 3000 Ci/mmol, PerkinElmer), 50 mM Tris/HCl (pH 7.5), and 1 mM EGTA, 1 mM Na$_3$VO$_4$, 1% 2-mercaptoethanol, 0.1% Brij 35, and 0.2 mg/ml BSA) in a final volume of 25 μL. Reactions were incubated at 30° C. for 30 min and stopped by adding 3% phosphoric acid, harvested onto a 96-well GF/B UniFilter (PerkinElmer) using a unifilter harvester (PerkinElmer), and counted with a TopCount microplate scintillation counter (PerkinElmer). The IC$_{50}$ values of inhibitors were determined after carrying out assays at 3-fold serially diluted concentrations of each compound in duplication. The results were analyzed using linear regression software (GraphPad Prism 4; GraphPad Software Inc.).

Inhibition activities of the selected compounds listed in Table 1 are summarized in Table 3. IC$_{50}$ value is defined as the concentration of the test compound which achieves a half-maximal inhibition of the kinase (B-Raf kinase) activity. + represents that the concentration (IC$_{50}$ value) is 10,000~1,000 nM; ++ represents that the concentration is 1,000-300 nM; and +++ represents that the concentration is less than 300 nM.

TABLE 3

| Cpd. ID | IC$_{50}$ ranking against B-Raf kinase |
|---|---|
| 1 | +++ |
| 2 | +++ |
| 3 | ++ |
| 4 | +++ |
| 5 | +++ |
| 6 | +++ |
| 7 | +++ |
| 8 | ++ |
| 9 | +++ |
| 10 | +++ |

TABLE 3-continued

| Cpd. ID | IC$_{50}$ ranking against B-Raf kinase |
|---|---|
| 11 | +++ |
| 12 | +++ |
| 13 | +++ |
| 14 | ++ |
| 15 | +++ |
| 16 | +++ |
| 17 | +++ |
| 18 | +++ |
| 19 | +++ |
| 20 | +++ |
| 21 | +++ |
| 22 | +++ |
| 23 | ++ |
| 24 | +++ |
| 25 | +++ |
| 26 | + |
| 27 | + |
| 28 | ++ |
| 29 | +++ |
| 30 | ++ |
| 31 | +++ |
| 32 | + |
| 33 | +++ |
| 34 | +++ |
| 35 | +++ |
| 36 | +++ |
| 37 | +++ |
| 38 | +++ |
| 39 | ++ |
| 40 | ++ |
| 41 | + |
| 42 | +++ |
| 43 | +++ |
| 44 | +++ |
| 45 | + |
| 46 | +++ |
| 47 | +++ |
| 48 | +++ |
| 49 | +++ |
| 50 | +++ |

2. B-Raf$^{V600E}$ Kinase Assay

Inhibition of kinase activity by a test compound disclosed herein was estimated by quantifying the amount of [$^{33}$P] incorporation of a substrate in the presence of the test compound. Standard assay conditions were 5 ng of recombinant B-Raf$^{V600E}$ kinase (Upstate Biotechnology) with 500 ng MEK1 (K97R) in assay buffer (8 μM ATP, 0.5 μCi [$^{33}$P]ATP (specific activity 3000 Ci/mmol, PerkinElmer), 50 mM Tris/HCl (pH 7.5), and 1 mM EGTA, 1 mM Na$_3$VO$_4$, 1% 2-mercaptoethanol, 0.1% Brij 35, and 0.2 mg/ml BSA), and the test compound (diluted with 4% DMSO) or DMSO alone (as a control) in a final volume of 25 μL. Reactions were incubated at 30° C. for 30 min and stopped by adding 3% phosphoric acid, harvested onto a 96-well GF/B Uni-Filter (PerkinElmer) using a unifilter harvester (PerkinElmer), and counted with a TopCount microplate scintillation counter (PerkinElmer). The IC$_{50}$ values of inhibitors were determined after carrying out assays at 3-fold serially diluted concentrations of each compound in duplication. The results were analyzed using linear regression software (GraphPad Prism 4; GraphPad Software Inc.).

Inhibition activities of the selected compounds listed in Table 1 are summarized in Table 4. IC$_{50}$ value is defined as the concentration of the test compound which achieves a half-maximal inhibition of the kinase (B-Raf$^{V600E}$ kinase) activity. + represents that the concentration (IC$_{50}$ value) is 10,000~1,000 nM; ++ represents that the concentration is 1,000-300 nM; and +++ represents that the concentration is less than 300 nM.

TABLE 4

| Cpd. ID | IC$_{50}$ ranking against B-Raf$^{V600E}$ kinase |
|---------|---------------------------------------------------|
| 1 | +++ |
| 2 | +++ |
| 3 | ++ |
| 4 | +++ |
| 5 | +++ |
| 6 | +++ |
| 7 | +++ |
| 8 | ++ |
| 9 | +++ |
| 10 | +++ |
| 11 | +++ |
| 12 | +++ |
| 13 | +++ |
| 14 | ++ |
| 15 | +++ |
| 16 | +++ |
| 17 | +++ |
| 18 | +++ |
| 19 | +++ |
| 20 | +++ |
| 21 | +++ |
| 22 | +++ |
| 23 | ++ |
| 24 | +++ |
| 25 | +++ |
| 26 | + |
| 27 | + |
| 28 | ++ |
| 29 | +++ |
| 30 | ++ |
| 31 | +++ |
| 33 | +++ |
| 34 | +++ |
| 35 | +++ |
| 36 | +++ |
| 37 | +++ |
| 38 | +++ |
| 39 | ++ |
| 40 | ++ |
| 41 | + |
| 42 | +++ |
| 43 | +++ |
| 44 | ++ |
| 45 | + |
| 46 | +++ |
| 47 | +++ |
| 48 | +++ |
| 49 | +++ |
| 50 | +++ |

3. C-Raf Kinase Assays

Inhibition of kinase activity by a test compound disclosed herein was estimated by quantifying the amount of [$^{33}$P] incorporation of a substrate in the presence of the test compound. Standard assay conditions were 2 ng of recombinant C-Raf kinase (Upstate Biotechnology) with 500 ng MEK1(K97R) in assay buffer (8 µM ATP, 0.5 µCi [$^{33}$P]ATP (specific activity 3000 Ci/mmol, PerkinElmer), 50 mM Tris/HCl (pH 7.5), and 1 mM EGTA, 1 mM Na$_3$VO$_4$, 1% 2-mercaptoethanol, 0.1% Brij 35, and 0.2 mg/ml BSA), and the test compound (diluted with 4% DMSO) or DMSO alone (as a control) in a final volume of 25 µL. Reactions were incubated at 30° C. for 30 min and stopped by adding 3% phosphoric acid, harvested onto a 96-well GF/B UniFilter (PerkinElmer) using a unifilter harvester (PerkinElmer), and counted with a TopCount microplate scintillation counter (PerkinElmer). The IC$_{50}$ values of inhibitors were determined after carrying out assays at 3-fold serially diluted concentrations of each compound in duplication. The results were analyzed using linear regression software (GraphPad Prism 4; GraphPad Software Inc.).

Inhibition activities of the selected compounds against B-Raf kinase are summarized in Table 5. IC$_{50}$ value is defined as the concentration of the test compound which achieves a half-maximal inhibition of the kinase (C-Raf kinase) activity. + represents that the concentration (IC$_{50}$ value) is 10,000~1,000 nM; ++ represents that the concentration is 1,000-300 nM; and +++ represents that the concentration is less than 300 nM.

TABLE 5

| Cpd. ID | IC$_{50}$ ranking against C-Raf kinase |
|---------|----------------------------------------|
| 1 | +++ |
| 2 | +++ |
| 3 | ++ |
| 4 | +++ |
| 5 | +++ |
| 6 | +++ |
| 7 | +++ |
| 8 | ++ |
| 9 | +++ |
| 10 | +++ |
| 11 | +++ |
| 12 | +++ |
| 13 | +++ |
| 14 | ++ |
| 15 | +++ |
| 16 | +++ |
| 17 | +++ |
| 18 | +++ |
| 19 | +++ |
| 20 | +++ |
| 21 | +++ |
| 22 | +++ |
| 23 | + |
| 24 | +++ |
| 25 | +++ |
| 26 | + |
| 27 | + |
| 28 | +++ |
| 29 | +++ |
| 30 | ++ |
| 31 | +++ |
| 33 | +++ |
| 34 | +++ |
| 35 | +++ |
| 36 | +++ |
| 37 | +++ |
| 38 | +++ |
| 39 | + |
| 40 | ++ |
| 41 | + |
| 42 | +++ |
| 43 | +++ |
| 44 | +++ |
| 45 | + |
| 46 | +++ |
| 47 | +++ |
| 48 | +++ |
| 49 | +++ |
| 50 | +++ |

4. Cell Proliferation Assay

As noted above, compounds of the invention may be used to treat protein kinase-related diseases or disorders. The protein kinase related disease may be cancer, diabetes, a renal disease, von Hip-pel-Lindau disease, fibrosis, osteoarthritis, an autoimmune disease, or a blood vessel proliferative disorder. The cancer may be lung cancer, colon cancer, colorectal cancer, breast cancer, prostate cancer, liver cancer, pancreatic cancer, bladder cancer, gastric cancer, renal cancer, salivary gland cancer, ovarian cancer, uterine body cancer, cervical cancer, oral cancer, skin cancer, brain cancer, lymphoma, or leukemia.

Inhibition of cell growth by compounds was measured using CELLTITER 96® assay. The cytotoxicity of compounds was evaluated in B-Raf$^{V600E}$ mutant A375 melanoma cell, B-Raf$^{V600E}$ mutant COLO205 colon cancer cell, and SK-MEL-2 melanoma cell with wild type B-Raf (B-Raf$^{wt}$) and NRAS$^{Q61R}$ mutation. A375 and COLO205 cell line were cultured in DMEM containing 10% FCS and incubated at 37° C. in 5% $CO_2$ atmosphere. SK-MEL-2 cell line was cultured in MEM containing 10% FCS and incubated at 37° C. in 5% $CO_2$ atmosphere. A375, COLO205 and SK-MEL-2 cell were seeded into 96-well plates at 2000, 2000, and 4000 cells/well, respectively, and allowed to adhere for overnight. Then, these seeded cells were treated with increasing concentrations of the test compounds and incubated for another 72 hours. At the end of the incubation, CELLTITER 96® Aqueous One Solution Reagent (Promega) was added and incubated for 4 hours. Cell viability was determined by measuring absorbance at 490 nm using EMAX® microplate reader (Molecular Devices).

The 50% inhibitory concentration ($IC_{50}$) value was calculated by plotting the percentage of growth inhibition against the concentration of compound, using GraphPad Prism5 software for curve fitting. The anti-proliferative activities of the selected compounds listed in Table 1 are summarized in Table 6. + represents that the concentration ($IC_{50}$ value) is 10,000~1,000 nM; ++ represents that the concentration is 1,000-300 nM; and +++ represents that the concentration is less than 300 nM.

TABLE 6

| | Cytotoxicity ($IC_{50}$ Ranking) | | |
|---|---|---|---|
| Cpd. ID | A375 (B-Raf$^{V600E}$) | COLO205 (B-Raf$^{V600E}$) | SK-MEL-2 (NRAS$^{Q61R}$, B-Raf$^{wt}$) |
| 1 | + | + | >10 μM |
| 2 | ++ | ++ | >10 μM |
| 4 | +++ | +++ | >10 μM |
| 5 | +++ | +++ | >10 μM |
| 6 | +++ | +++ | >10 μM |
| 7 | +++ | +++ | >10 μM |
| 8 | + | + | >10 μM |
| 9 | +++ | +++ | >10 μM |
| 10 | +++ | +++ | >10 μM |
| 11 | ++ | + | >10 μM |
| 12 | + | ++ | >10 μM |
| 13 | ++ | + | >10 μM |
| 14 | + | + | >10 μM |
| 15 | ++ | ++ | >10 μM |
| 16 | +++ | +++ | >10 μM |
| 17 | +++ | +++ | >10 μM |
| 18 | +++ | +++ | >10 μM |
| 19 | +++ | +++ | >10 μM |
| 20 | +++ | +++ | >10 μM |
| 21 | +++ | +++ | >10 μM |
| 22 | +++ | +++ | >10 μM |
| 23 | +++ | +++ | >10 μM |
| 24 | ++ | +++ | >10 μM |
| 25 | ++ | +++ | >10 μM |
| 26 | + | + | >10 μM |
| 27 | + | ++ | >10 μM |
| 28 | ++ | +++ | >10 μM |
| 29 | +++ | +++ | >10 μM |
| 30 | + | + | >10 μM |
| 31 | ++ | ++ | >10 μM |
| 33 | +++ | +++ | + |

TABLE 6-continued

| | Cytotoxicity ($IC_{50}$ Ranking) | | |
|---|---|---|---|
| Cpd. ID | A375 (B-Raf$^{V600E}$) | COLO205 (B-Raf$^{V600E}$) | SK-MEL-2 (NRAS$^{Q61R}$, B-Raf$^{wt}$) |
| 34 | +++ | +++ | >10 μM |
| 35 | +++ | +++ | >10 μM |
| 36 | +++ | +++ | >10 μM |
| 37 | + | + | >10 μM |
| 38 | +++ | +++ | >10 μM |
| 39 | + | + | >10 μM |
| 40 | + | + | >10 μM |
| 41 | + | + | >10 μM |
| 42 | +++ | +++ | >10 μM |
| 43 | +++ | +++ | >10 μM |
| 44 | ++ | ++ | >10 μM |
| 46 | +++ | +++ | >10 μM |
| 47 | +++ | +++ | >10 μM |
| 48 | +++ | +++ | >10 μM |
| 49 | +++ | +++ | >10 μM |
| 50 | +++ | +++ | >10 μM |

Data in Table 6 clearly show that compounds of the invention can inhibit cancer cell growth, particular in cancer cell expressing B-Raf mutant. Therefore, these compounds may be used in the treatment of cancers.

Some embodiments of the invention relate to methods for treating a protein kinase-related disease. A method in accordance with one embodiment of the invention comprises administering to a subject in need thereof an effective amount of a compound of the invention.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A compound of formula (I):

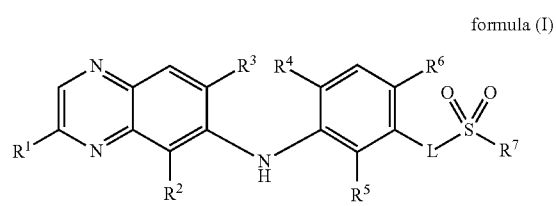

formula (I)

or a stereoisomer, a tautomer, a pharmaceutically acceptable salt thereof, wherein L is $NR^8$ or O;

$R^1$ is selected from the group consisting of hydrogen, halogen, $NR^9R^{10}$, $OR^{11}$, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, phenyl, a 3-to-6 membered heterocyclyl, and a 5-to-6 membered heteroaryl, wherein the alkyl, alkenyl, alkynyl, cycloakyl, phenyl, heterocyclyl, and heteroaryl are optionally substituted with halogen, oxo (except for phenyl or heteroaryl), $OR^a$, $SR^a$, $NR^bR^c$, phenyl, $C_1$-$C_4$ alkyl, $C_1$-$C_4$ alkoxy, and cyclopropyl, wherein the alkyl, alkoxy, and cyclopropyl are optionally substituted with $R^d$;

$R^2$ is selected from the group consisting of nitro, CN, $OR^{11}$, and $COR^{12}$;

$R^3$ is selected from the group consisting of hydrogen, halogen, hydroxy, azido, cyano, nitro, $C_2$-$C_6$ alkenyl, $C_2$-$C_6$ alkynyl, $C_3$-$C_6$ cycloalkyl, phenyl, a 3-to-6 membered heterocyclyl, and a 5-to-6 membered heteroaryl, wherein the alkyl, alkenyl, alkynyl, cycloakyl, phenyl, heterocyclyl, and heteroaryl are optionally substituted with halogen, oxo (except for phenyl or heteroaryl), $OR^a$, $SR^a$, $NR^bR^c$, phenyl, $C_1$-$C_4$ alkyl, $C_1$-$C_4$ alkoxy, and cyclopropyl, wherein the alkyl, alkoxy, and cyclopropyl are optionally substituted with $R^d$, provided that $R^3$ is hydrogen or halogen only when $R^1$ is $NR^9R^{10}$ and $R^9$ and $R^{10}$ are not hydrogen or $C_1$-$C_4$ alkyl;

$R^4$, $R^5$ and $R^6$ are independently selected from the group consisting of hydrogen, halogen, hydroxyl, amino, CN, $C_1$-$C_4$ alkyl, alkoxy $C_1$-$C_4$ alkoxy, dialkylamino, $C_1$-$C_4$ alkoxy, and heterocyclyl;

$R^7$ is $C_1$-$C_4$ alkyl, $C_1$-$C_4$ haloalkyl, or aryl;

$R^8$ is selected from the group consisting of hydrogen, $SO_2R^{15}$, $C_1$-$C_6$ alkyl, $C_2$-$C_6$ alkenyl, $C_2$-$C_6$ alkynyl, $C_3$-$C_6$ cycloalkyl and a 3-to-6 membered heterocyclyl, wherein the alkyl, alkenyl, alkynyl, cycloakyl and heterocyclyl are optionally substituted with halogen, oxo (except for phenyl or heteroaryl), $OR^a$, $SR^a$, $NR^bR^c$, phenyl, $C_1$-$C_4$ alkyl, $C_1$-$C_4$ alkoxy, and cyclopropyl, wherein the alkyl, alkoxy, and cyclopropyl are optionally substituted with $R^d$;

$R^9$ and $R^{10}$ are independently selected from the group consisting of hydrogen, $COR^{15}$, $SO_2R^{15}$, $OR^{16}$, $NR^{17}R^{18}$, $C_1$-$C_6$ alkyl, $C_2$-$C_6$ alkenyl, $C_2$-$C_6$ alkynyl, $C_3$-$C_6$ cycloalkyl, phenyl, a 3-to-6 membered heterocyclyl, and a 5-to-6 membered heteroaryl, wherein the alkyl, alkenyl, alkynyl, cycloakyl, phenyl, heterocyclyl, and heteroaryl are optionally substituted with halogen, oxo (except for phenyl or heteroaryl), $OR^a$, $SR^a$, $NR^bR^c$, phenyl, $C_1$-$C_4$ alkyl, $C_1$-$C_4$ alkoxy, and cyclopropyl, wherein the alkyl, alkoxy, and cyclopropyl are optionally substituted with $R^d$;

$R^9$ and $R^{10}$, together with the nitrogen atom to which they are attached, form a 3-to-6 membered heterocyclyl, which is optionally substituted by halogen, oxo or $C_1$-$C_3$ alkyl;

$R^{11}$ is selected from the group consisting of hydrogen, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, phenyl, a 3-to-6 membered heterocyclyl, and a 5-to-6 membered heteroaryl, wherein the alkyl, alkenyl, alkynyl, cycloakyl, phenyl, heterocyclyl, and heteroaryl are optionally substituted with halogen, oxo (except for phenyl or heteroaryl), $OR^a$, $SR^a$, $NR^bR^c$, phenyl, $C_1$-$C_4$ alkyl, $C_1$-$C_4$ alkoxy, and cyclopropyl, wherein the alkyl, alkoxy, and cyclopropyl are optionally substituted with $R^d$;

$R^{12}$ is selected from the group consisting of hydrogen, $OR^{19}$, $NR^{20}R^{21}$, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, phenyl, a 3-to-6 membered heterocyclyl, and a 5-to-6 membered heteroaryl, wherein the alkyl, alkenyl, alkynyl, cycloakyl, phenyl, heterocyclyl, and heteroaryl are optionally substituted with halogen, oxo (except for phenyl or heteroaryl), $OR^a$, $SR^a$, $NR^bR^c$, phenyl, $C_1$-$C_4$ alkyl, $C_1$-$C_4$ alkoxy, and cyclopropyl, wherein the alkyl, alkoxy, and cyclopropyl are optionally substituted with $R^d$, $R^{15}$ is selected from the group consisting of $C_1$-$C_4$ alkyl, $C_1$-$C_4$ haloalkyl, and aryl;

$R^{16}$ is selected from the group consisting of hydrogen, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, phenyl, a 3-to-6 membered heterocyclyl, and a 5-to-6 membered heteroaryl, wherein the alkyl, alkenyl, alkynyl, cycloakyl, phenyl, heterocyclyl, and heteroaryl are optionally substituted with halogen, oxo (except for phenyl or heteroaryl), $OR^a$, $SR^a$, $NR^bR^c$, phenyl, $C_1$-$C_4$ alkyl, $C_1$-$C_4$ alkoxy, and cyclopropyl, wherein the alkyl, alkoxy, and cyclopropyl are optionally substituted with $R^d$;

$R^{17}$ and $R^{18}$ are independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, phenyl, a 3-to-6 membered heterocyclyl, and a 5-to-6 membered heteroaryl, wherein the alkyl, alkenyl, alkynyl, cycloakyl, phenyl, heterocyclyl, and heteroaryl are optionally substituted with halogen, oxo (except for phenyl or heteroaryl), $OR^a$, $SR^a$, $NR^bR^c$, phenyl, $C_1$-$C_4$ alkyl, $C_1$-$C_4$ alkoxy, and cyclopropyl, wherein the alkyl, alkoxy, and cyclopropyl are optionally substituted with $R^d$, $R^{19}$ is selected from the group consisting of hydrogen, $C_1$-$C_4$ alkyl, $C_1$-$C_4$ haloalkyl, and aryl;

$R^{20}$ and $R^{21}$ are independently selected from the group consisting of hydrogen, $C_1$-$C_4$ alkyl, $C_1$-$C_4$ haloalkyl, and aryl;

wherein each $R^a$ is independently hydrogen or $C_1$-$C_4$ alkyl;

wherein each $R^b$ and $R^c$ are independently selected from the group consisting of hydrogen, $SO_2R^7$ and $C_1$-$C_4$ alkyl, wherein the $C_1$-$C_4$ alkyl is optionally substituted with halogen;

wherein each $R^d$ is independently selected from the group consisting of halogen, oxo, $C_1$-$C_4$ alkyl, and $C_1$-$C_4$ alkoxyl, wherein the $C_1$-$C_4$ alkyl and $C_1$-$C_4$ alkoxyl are optionally substituted with halogen.

2. The compound of claim 1, wherein $R^3$ is hydrogen.
3. The compound of claim 1, wherein L is NH.
4. The compound of claim 1, wherein $R^6$ is hydrogen.
5. The compound of claim 1, wherein $R^4$ and $R^5$ are fluorine.
6. The compound of claim 1, where the compound is:
N1-{2,4-difluoro-3-[(3-methoxy-5-nitro-6-quinoxalinyl)amino]phenyl}-1-propanesulfonamide;
N1-{2,4-difluoro-3-[(3-methoxy-5-nitro-6-quinoxalinyl)amino]phenyl}-3-fluoro-1-propanesulfonamide;
N1-(2,4-difluoro-3-{[3-(2-morpholinoethoxy)-5-nitro-6-quinoxalinyl]amino}phenyl)-1-propanesulfonamide;
N1-(2,4-difluoro-3-[3-(2-methoxyethoxy)-5-nitro-6-quinoxalinyl]aminophenyl)-1-propanesulfonamide;
N1-[3-({3-[2-(dimethylamino)ethoxy]-5-nitro-6-quinoxalinyl}amino)-2,4-difluorophenyl]-1-propanesulfonamide;
N1-{3-[(5-cyano-3-methoxy-6-quinoxalinyl)amino]-2,4-difluorophenyl}-1-propanesulfonamide;
N-{2,4-difluoro-3-[(3-methoxy-5-nitro-6-quinoxalinyl)amino]phenyl}methanesulfonamide;
N1-{3-[(5-cyano-3-hydroxy-6-quinoxalinyl)amino]-2,4-difluorophenyl}-1-propanesulfonamide;
N1-(3-{[5-cyano-3-(2-morpholinoethoxy)-6-quinoxalinyl]amino}-2,4-difluorophenyl)-1-propanesulfonamide;
N-(3-(5-cyano-3-ethoxyquinoxalin-6-ylamino)-2,4-difluorophenyl)propane-1-sulfonamide;
N-(3-(5-cyano-3-(dimethylamino)quinoxalin-6-ylamino)-2,4-difluorophenyl)propane-1-sulfonamide;
N-(3-(5-cyano-3-morpholinoquinoxalin-6-ylamino)-2,4-difluorophenyl)propane-1-sulfonamide;
N-(3-(5-cyano-3-(methylamino)quinoxalin-6-ylamino)-2,4-difluorophenyl)propane-1-sulfonamide;
N-(3-(5-cyano-3-methoxyquinoxalin-6-ylamino)-2,6-difluorophenyl)propane-1-sulfonamide;

N-(5-(5-cyano-3-methoxyquinoxalin-6-ylamino)-2-fluorophenyl)propane-1-sulfonamide;
N-(3-(5-cyano-3-morpholinoquinoxalin-6-ylamino)-4-fluorophenyl)propane-1-sulfonamide;
N-(3-(5-cyano-3-ethoxyquinoxalin-6-ylamino)-4-fluorophenyl)benzenesulfonamide;
N-(3-(5-cyano-3-morpholinoquinoxalin-6-ylamino)-4-fluorophenyl)benzenesulfonamide;
N-(3-(5-cyano-3-morpholinoquinoxalin-6-ylamino)-4-fluorophenyl)methanesulfonamide;
N-(3-(5-cyano-3-ethoxyquinoxalin-6-ylamino)-4-fluorophenyl)methanesulfonamide;
N-(3-(5-cyano-3-(dimethylamino)quinoxalin-6-ylamino)-4-fluorophenyl)propane-1-sulfonamide;
N-(2,4-difluoro-3-(5-formyl-3-methoxyquinoxalin-6-ylamino)phenyl)propane-1-sulfonamide;
6-(2,6-difluoro-3-(propylsulfonamido)phenylamino)-3-methoxyquinoxaline-5-carboxylic acid;
methyl 6-(2,6-difluoro-3-(propylsulfonamido)phenylamino)-3-methoxyquinoxaline-5-carboxylate;
N-(3-(5-cyano-3-morpholinoquinoxalin-6-ylamino)-2,4-difluorophenyl)-3-fluoropropane-1-sulfonamide;
N-(3-(5-cyano-3-ethoxyquinoxalin-6-ylamino)-2,4-difluorophenyl)-3-fluoropropane-1-sulfonamide;
N-(3-(5-cyano-3-methoxyquinoxalin-6-ylamino)-4-fluorophenyl)benzenesulfonamide;
N-(3-(5-cyano-3-ethoxyquinoxalin-6-ylamino)-4-fluorophenyl)propane-1-sulfonamide;
N-(3-(5-cyano-3-(dimethylamino)quinoxalin-6-ylamino)-4-fluorophenyl)benzenesulfonamide;
N-(3-(5-cyano-3-morpholinoquinoxalin-6-ylamino)-2-methylphenyl)propane-1-sulfonamide;
N-(3-(5-cyano-3-morpholinoquinoxalin-6-ylamino)-4-methylphenyl)propane-1-sulfonamide;
N-(3-(5-cyano-3-methoxyquinoxalin-6-ylamino)-4-methylphenyl)propane-1-sulfonamide;
N-(3-(5-cyano-3-methoxyquinoxalin-6-ylamino)-4-fluorophenyl)methanesulfonamide;
N-(3-(5-cyano-3-methoxyquinoxalin-6-ylamino)-2,4-difluorophenyl)-N-ethylpropane-1-sulfonamide;
N-(3-(5-cyano-3-methoxyquinoxalin-6-ylamino)-2,4-difluorophenyl)-N-methylpropane-1-sulfonamide;
N-(3-(5-cyano-3-methoxyquinoxalin-6-ylamino)-2-methylphenyl)propane-1-sulfonamide;
N-(5-(5-cyano-3-methoxyquinoxalin-6-ylamino)-2-methylphenyl)propane-1-sulfonamide;
N-(2-chloro-3-(5-cyano-3-methoxyquinoxalin-6-ylamino)-4-fluorophenyl)propane-1-sulfonamide;
N-(2-chloro-3-(5-cyano-3-methoxyquinoxalin-6-ylamino)-4-fluorophenyl)benzenesulfonamide;
N-(2-chloro-3-(5-cyano-3-morpholinoquinoxalin-6-ylamino)-4-fluorophenyl)propane-1-sulfonamide;
N-(2-chloro-3-(5-cyano-3-morpholinoquinoxalin-6-ylamino)-4-fluorophenyl) benzenesulfonamide; or
N-(2-cyano-3-(5-cyano-3-methoxyquinoxalin-6-ylamino)phenyl) propane-1-sulfonamide.

7. A pharmaceutical composition, comprising a compound of claim 1, a salt thereof, a stereoisomer thereof, or a pro-drug thereof; and a pharmaceutically acceptable carrier.

8. A method for treating a RAF kinase-related cancer, comprising administering to a subject in need thereof an effective amount of the compound of claim 1, wherein the RAF kinase-related cancer is melanoma or colon cancer.

9. The method of claim 8, wherein $R^3$ is hydrogen.

10. The method of claim 9, wherein L is NH.

11. The method of claim 8, wherein $R^6$ is hydrogen.

12. The compound of claim 2, wherein $R^6$ is hydrogen.

13. The compound of claim 3, wherein $R^6$ is hydrogen.

14. The compound of claim 2, wherein $R^4$ and $R^5$ are fluorine.

15. The compound of claim 3, wherein $R^4$ and $R^5$ are fluorine.

16. The compound of claim 4, wherein $R^4$ and $R^5$ are fluorine.

* * * * *